United States Patent
Bønsdorff et al.

(10) Patent No.: US 9,782,500 B2
(45) Date of Patent: Oct. 10, 2017

(54) MONOCLONAL ANTIBODY AND DERIVATIVES

(71) Applicant: Oncoinvent AS, Oslo (NO)

(72) Inventors: Tina Bjørnlund Bønsdorff, Oslo (NO); Roy Hartvig Larsen, Oslo (NO)

(73) Assignee: Oncoinvent AS, Oslo (NO)

( * ) Notice: Subject to any disclaimer, the term of this patent is extended or adjusted under 35 U.S.C. 154(b) by 0 days.

(21) Appl. No.: 14/915,134

(22) PCT Filed: Sep. 24, 2014

(86) PCT No.: PCT/EP2014/070395
§ 371 (c)(1),
(2) Date: Feb. 26, 2016

(87) PCT Pub. No.: WO2015/044218
PCT Pub. Date: Apr. 2, 2015

(65) Prior Publication Data
US 2016/0206764 A1      Jul. 21, 2016

(30) Foreign Application Priority Data

Sep. 24, 2013   (DK) .................................. 2013 70532

(51) Int. Cl.
| | |
|---|---|
| *A61K 51/10* | (2006.01) |
| *C07K 16/30* | (2006.01) |
| *C07K 16/00* | (2006.01) |
| *C07K 16/28* | (2006.01) |
| *A61K 45/06* | (2006.01) |
| *A61K 39/00* | (2006.01) |

(52) U.S. Cl.
CPC .......... *A61K 51/1045* (2013.01); *A61K 45/06* (2013.01); *A61K 51/10* (2013.01); *A61K 51/1027* (2013.01); *A61K 51/1051* (2013.01); *A61K 51/1066* (2013.01); *C07K 16/2803* (2013.01); *C07K 16/2821* (2013.01); *C07K 16/30* (2013.01); *C07K 16/3015* (2013.01); *C07K 16/3053* (2013.01); *C07K 16/3092* (2013.01); *A61K 2039/505* (2013.01); *A61K 2039/507* (2013.01); *C07K 2317/24* (2013.01); *C07K 2317/56* (2013.01); *C07K 2317/732* (2013.01); *C07K 2317/92* (2013.01)

(58) Field of Classification Search
CPC .... A61K 51/10; A61K 51/1045; C07K 16/30; C07K 16/00
USPC ..................................... 530/388.1; 424/133.1
See application file for complete search history.

(56) References Cited

U.S. PATENT DOCUMENTS

| | | |
|---|---|---|
| 6,824,995 B1 | 11/2004 | Wu |
| 2011/0171229 A1 | 7/2011 | Ferrone et al. |
| 2011/0200608 A1 | 8/2011 | Wang et al. |

FOREIGN PATENT DOCUMENTS

WO       WO 03/057838 A2       7/2003

OTHER PUBLICATIONS

Campoli, Michael et al., "Functional and Clinical Relevance of Chondroitin Sulfate Proteoglycan 4" Advances in Cancer Research, 2010, pp. 73-121.
Ma, Xiaoli "Synergistic Killing Effect between Vorinostat and Target of CD146 in Malignant Cells" Clin. Cancer Res., 2010, pp. 5165-5176, vol. 16, No. 21.
McGARY, Eric C. et al., "A Fully Human Antimelanoma Cellular Adhesion Molecule/MUC18 Antibody Inhibits Spontaneous Pulmonary Metastasis of Osteosarcoma Cells In Vivo" Clinical Cancer Research, Dec. 15, 2003, pp. 6560-6566, vol. 9.
Zhang, Ying et al., "Generation and Characterization of a Panel of Monoclonal Antibodies Against Distinct Epitopes of Human CD146" Hybridoma, 2008, pp. 345-352, vol. 27, No. 5.
International Search Report for PCT/EP2014/070395 dated Dec. 9, 2014.

*Primary Examiner* — Yan Xiao
(74) *Attorney, Agent, or Firm* — Knobbe Martens Olson & Bear LLP

(57) ABSTRACT

The present invention relates to a novel anti-CD146 antibody and derivatives thereof. The antibody and/or derivatives can be used for therapy and/or imaging, diagnosis and/or immunostaining.

7 Claims, 11 Drawing Sheets

SEQUENCE LISTING

```
<160> NUMBER OF SEQ ID NOS: 7

<210> SEQ ID NO 1
<211> LENGTH: 414
<212> TYPE: DNA
<213> ORGANISM: Mus musculus

<400> SEQUENCE: 1
atgggatgga tctggttctt tctcttcctc ctgtcaggaa ctgcaggtgt ccactctgag      60
gtccagttgc agcagtctgg acctgagcta gtgaagactg gggcttcagt gaagatatcc     120
tgcaaggctt ctggttactc attcactggt tactacatac actgggtcaa gcagagccat     180
ggaaagagcc ttgagtggat tggatatatt agtaattaca atggtgctac tacctacagc     240
caggagttca agggcaaggc cacatttact gtagacagat cctccaggat agcctacatg     300
cagttcaccg gcctgacatc tgaagactct gcggtctatt actgtgcggg taacagctgg     360
```
ggtgactggt acttcgatgt ctggggcgca gggaccacgg tcaccgtctc ctca          414

<210> SEQ ID NO 2
<211> LENGTH: 390
<212> TYPE: DNA
<213> ORGANISM: Mus musculus

<400> SEQUENCE: 2
atgaagttgc ctgttaggct gttggtgctg atgttctgga ttcctgcttc cagcagtgat     60
gttgtgatga cccaaactcc actctccctg cctgtcagtc ttggagatca agcctccatc    120
gttgtgatga cccaaactcc actctccctg cctgtcagtc ttggagatca agcctccatc    180
ctgcagaagc caggccagtc tccaaagctc ctgatctaca agtttccaa ccgatttcct    240 ggggtcccag acaggttcag tgcagtgga tcagggacag atttcacact caagatcagc    300
agagtggagg ctgaggatct gggagtttat ttctgctctc aaagtacaca tgtttccacg    360
ttcggagggg ggaccaagct ggaaataaaa                                      390

<210> SEQ ID NO 3
<211> LENGTH: 138
<212> TYPE: PRT
<213> ORGANISM: Mus musculus

<400> SEQUENCE: 3

Met Gly Trp Ile Trp Phe Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Thr Gly Ala Ser Val Lys Ile Ser Cys Lys Ala Ser Gly Tyr Ser Phe
        35                  40                  45

Thr Gly Tyr Tyr Ile His Trp Val Lys Gln Ser His Gly Lys Ser Leu
    50                  55                  60

Glu Trp Ile Gly Tyr Ile Ser Asn Tyr Asn Gly Ala Thr Thr Tyr Ser
65                  70                  75                  80

Gln Glu Phe Lys Gly Lys Ala Thr Phe Thr Val Asp Arg Ser Ser Arg
                85                  90                  95

Ile Ala Tyr Met Gln Phe Thr Gly Leu Thr Ser Glu Asp Ser Ala Val
            100                 105                 110

Tyr Tyr Cys Ala Gly Asn Ser Trp Gly Asp Trp Tyr Phe Asp Val Trp
        115                 120                 125

Gly Ala Gly Thr Thr Val Thr Val Ser Ser
    130                 135

<210> SEQ ID NO 4
<211> LENGTH: 130
<212> TYPE: PRT
<213> ORGANISM: Mus musculus

<400> SEQUENCE: 4

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Thr Tyr Leu His Trp Tyr Leu Gln Lys Pro
    50                  55                  60

```
Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Phe Cys
            100                 105                 110

Ser Gln Ser Thr His Val Ser Thr Phe Gly Gly Gly Thr Lys Leu Glu
        115                 120                 125

Ile Lys
    130

<210> SEQ ID NO 5
<211> LENGTH: 321
<212> TYPE: DNA
<213> ORGANISM: Homo sapiens

<400> SEQUENCE: 5
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                               321

<210> SEQ ID NO 6
<211> LENGTH: 990
<212> TYPE: DNA
<213> ORGANISM: Homo sapiens

<400> SEQUENCE: 6
gcctccacca agggaccaag cgtgttccca ctggctccat ctagtaaaag tacttcaggg      60 ggaccgccg ctctgggatg tctggtgaag gattatttcc cagagcccgt gacagtgagc     120
tggaactccg gcgccctgac ctccggagtg cacacatttc cagctgtgct gcagtcaagc     180
ggcctgtact ctctgtcctc tgtggtgacc gtgcccagtt caagcctggg gactcagacc     240
tatatctgca acgtgaatca caagccaagt aatacaaaag tggacaagaa agtggaaccc     300
aagagctgtg ataaaacaca tacttgcccc ccttgtcctg ctccagagct gctgggagga     360
ccaagcgtgt tcctgtttcc acccaagcct aaagacaccc tgatgatttc aggacacccc     420
gaagtgactt gcgtggtggt ggacgtgtct cacgaggatc ctgaagtgaa gttcaactgg     480
tacgtggatg gcgtggaggt gcataatgcc aagaccaaac ccagggagga acagtacaat     540
agcacctatc gcgtggtgtc cgtgctgaca gtgctgcacc aggactggct gaacggcaaa     600
gagtataagt gcaaagtgag caataaggcc ctgcccgctc tatcgagaa acaattagc      660 aaggccaaag ggcagcctcg ggaaccacag gtgtacactc tgcctccatc cagagacgag     720
ctgacaaaga accaggtgtc tctgacttgt ctggtgaaag gttctatcc ttcagatatt     780 gctgtggagt gggaaagcaa tggacagcca gaaacaatt acaagaccac acccctgtg     840 ctggactctg atggaagttt ctttctgtat tctaagctga ctgtggataa agtcggtgg      900 cagcagggca acgtgtttag ctgttccgtg atgcatgagg ccctgcacaa tcattacacc     960
cagaagtctc tgagtctgtc acctggcaaa                                     990
```

```
<210> SEQ ID NO 7
<211> LENGTH: 1041
<212> TYPE: DNA
<213> ORGANISM: Homo sapiens

<400> SEQUENCE: 7
gctagcacca agggcccatc ggtcttcccc ctggcgccct gctccaggag cacccctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacacctgca acgtgaatca caagcccagc aacaccaagg tggacaagag agttgagctc     300 aaaacccac ttggtgacac aactcacaca tgcccacggt gcccagagcc caaatcttgt      360
gacacacctc cccatgccc acggtgccca gcacctgaac tcctggggag accgtcagtc      420
ttcctcttcc cccaaaacc caaggatacc cttatgattt cccggacccc tgaggtcacg      480
tgcgtggtgg tggacgtgag ccacgaagac cccgaggtcc agttcaagtg gtacgtggac     540
ggcgtggagg tgcataatgc caagacaaag ccgcgggagg agcagttcaa cagcacgttc     600
cgtgtggtca gcgtcctcac cgtcctgcac caggactggc tgaacggcaa ggagtacaag     660
tgcaaggtct ccaacaaagc cctcccagcc cccatcgaga aaccatctc caaaaccaaa      720 ggacagcccc gagaaccaca ggtgtacacc ctgcccccat cccggagga tgaccaag      780 aaccaggtca gcctgacctg cctggtcaaa ggcttctacc ccagcgacat cgccgtggag     840
tgggagagca gcgggcagcc ggagaacaac tacaacacca cgcctcccat gctggactcc     900
gacggctcct tcttcctcta cagcaagctc accgtggaca gagcaggtg gcagcagggg     960 aacgtcttct catgctccgt gatgcatgag gctctgcaca accactacac gcagaagagc    1020
ctctccctgt ctccgggtaa a                                              1041
```

MONOCLONAL ANTIBODY AND DERIVATIVES

CROSS REFERENCE TO RELATED APPLICATIONS

Figure 1:
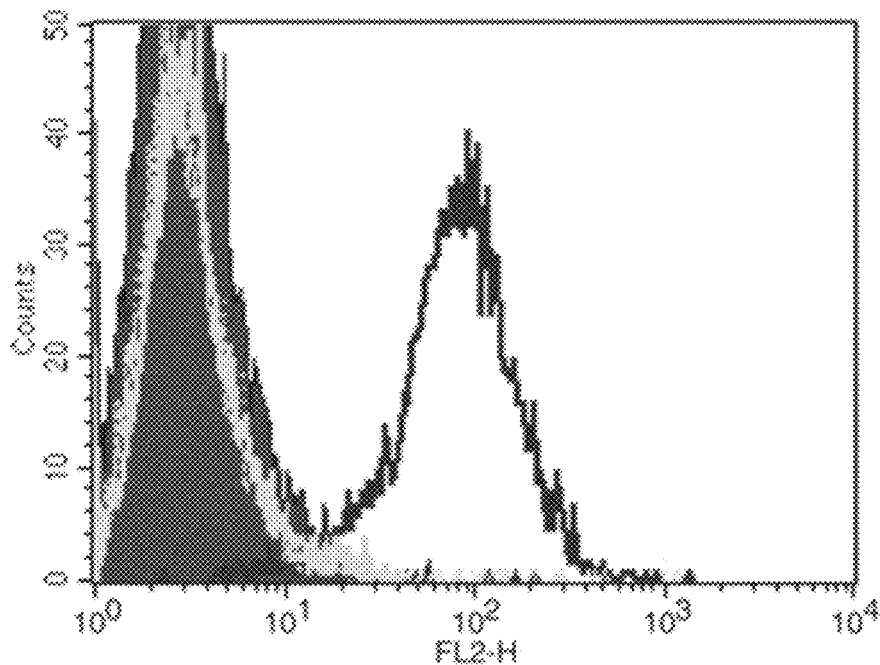

This application is a U.S. National Phase Application of PCT International Application Number PCT/EP2014/070395, filed on Sep. 24, 2014, designating the United States of America and published in the English language, which is an International Application of and claims the benefit of priority to Danish Patent Application No. PA 2013 70532, filed on Sep. 24, 2013. The disclosures of the above-referenced applications are hereby expressly incorporated by reference in their entireties.

TECHNICAL FIELD OF THE INVENTION

The present invention relates to a novel anti-CD146 (melanoma cell adhesion molecule (MCAM) or cell surface glycoprotein MUC18) antibody and derivatives thereof. The antibody and/or derivatives can be used for therapy and/or imaging, diagnosis and/or immunostaining and/or immunopurging.

BACKGROUND OF THE INVENTION

An interesting tumor associated antigen which could be used as target in antibody therapy is the CD146 antigen.

CD146 (cluster of differentiation 146) also known as the melanoma cell adhesion molecule (MCAM) or cell surface glycoprotein MUC18, is a 113 kDa cell adhesion molecule currently used as a marker for endothelial cell lineage. In humans, the CD146 protein is encoded by the MCAM gene.

Upregulation of this antigen was first described for malignant cells of melanocytic lineage (Lehmann et al., 1987) and later it was found to be a marker of disease progression in malignant melanoma (Lehmann, et al., 1989). The expression of this antigen was found to be up-regulated in several cancer forms, including melanoma, prostate cancer, breast cancer, mesothelioma, pancreatic carcinoma, osteosarcoma and lung cancer (Sers et al., 1994; Filshie, et al., 1998; Wu et al., 1998; Kristiansen et al., 2003; McGary et al, 2003; Aldovini et al., 2006; Bidlingmaier et al, 2009). It is also observed in association with inflammation (Middleton et al 2005; Bardin et al., 2006). In normal mature tissues, expression of CD146 is found on endothelial cells, smooth muscle cells, a subpopulation of activated T-lymphocytes and intermediate trophoblasts (Pickl et al., 1997; Shih et al., 1996; Sers et al., 1994). Thus CD146 could be a target for cancer therapy.

The use of monoclonal antibodies has increased steadily since its discovery in the 1970s and today it is a multi-billion industry. Antibody based treatments have been developed against a number of cancer associated antigens including Her-2 and CD20 and today monoclonal antibodies constitutes an important class of therapeutics.

The mechanisms of action of monoclonal antibodies in targeted therapy are diverse. Some therapeutic antibodies act by arresting proliferation of target cell by binding to the target antigen receptor on the cell surface. Other monoclonal antibodies have been developed (chimeric, humanized, fully human) to interact with human immune effectors (e.g. complement factors, Natural Killer cells) to stimulate targeted tumor cell kill by these immune effectors. Monoclonal antibodies can be further developed as targeting entities by conjugation to nanoparticles or microparticles made from polymers or proteins or inorganic crystals or a combination thereof, carrying cytotoxic drugs or radioactive molecules. The monoclonal antibodies can also be directly conjugated to drugs (Antibody Drug Conjugates) (Sinha et al., 2006, Peer et al., 2007, Sievers &.Senter, 2013)

Monoclonal antibodies have been developed against the CD146 antigen in the past and in vitro and in vivo testing of targeting with anti-CD146 monoclonal antibodies has shown a considerable promise (McGary et al., 2003; Melnikova et al., 2006; Ma et al., 2010). Although the function of CD146 is not fully understood, proliferative function has been shown to be inhibited by antibody binding, and CD146 has been described as a new co-receptor for VEGFR-2 and a promising target for blocking tumor-related angiogenesis (Jiang et al., 2012). CD146 has also been studied as a potential antigen for targeted-internalizing immunoliposome-technology (Iyer et al, 2011).

SUMMARY IN THE INVENTION

A new monoclonal antibody, OI-3, and derivatives of, that target an epitope on CD146 with a broad expression on tumor cells of various origins.

The OI-3 shows a significant specific binding on cells pre-blocked with other commercial available anti-CD146 antibodies, indicating a substantial uniqueness of the epitope that OI-3 combines with.

OI-3 is also distinguished by the ability to altogether bind to cells, frozen tissue sections and paraffin-embedded tissue samples signifying the targeting of a versatile and robust epitope compared with some of the CD146 antibodies sited in the literature (Zhang et al., 2008).

It also shows superiority to well-known CSPG4 targeting antibodies in binding to cells co-expressing both CD146 and CSPG4, including melanoma, osteosarcoma and triple negative breast cancer.

An aspect of the present invention relates to an antibody molecule that binds to human CD146 and that is a monoclonal antibody that is defined by a variable heavy chain comprising the amino acid sequence shown in SEQ ID NO: 3; and a variable light chain comprising the amino acid sequence shown in SEQ ID NO: 4, or a monoclonal antibody recognizing the same epitope of human CD146 as the antibody defined in a) or recognizing an epitope that is close to or overlaps with said epitope, or a monoclonal antibody that share at least 80% of epitope combining sequence identity with the antibodies defined above.

In one embodiment of the present invention is the antibody the monoclonal antibody OI-3.

Another aspect of the present invention relates to an antibody molecule that binds to human CD146 and that is derived from a monoclonal antibody that is defined by a variable heavy chain comprising the amino acid sequence shown in SEQ ID NO: 3; and a variable light chain comprising the amino acid sequence shown in SEQ ID NO: 4, or from a non-human antibody recognizing the same epitope of human CD146 as the antibody defined in a) or recognizing an epitope that is close to or overlaps with said epitope; wherein said antibody molecule is a chimeric or a humanized antibody.

Yet another aspect of the present invention relates to a radioimmunoconjugate that binds human CD146 comprising an antibody of the present invention, a linker, and a radionuclide selected from the group consisting of $^{211}$At, $^{213}$Bi, $^{212}$Bi, $^{212}$Pb, $^{225}$Ac, $^{227}$Th, $^{90}$Y, $^{186}$Re, $^{188}$Re, $^{199}$Au, $^{194}$Ir, $^{166}$Ho, $^{159}$Gd, $^{153}$Sm, $^{149}$Pm, $^{142}$Pr, $^{111}$Ag, $^{109}$Pd, $^{77}$As, $^{67}$Cu, $^{47}$Sc, $^{230}$U, $^{226}$Th, $^{223}$Ra, $^{224}$Ra, $^{225}$Ra, $^{131}$I, $^{18}$F, $^{64}$Cu, $^{67}$Ga, $^{99m}$Tc, $^{123}$I, $^{124}$I, $^{125}$I, $^{131}$I, $^{111}$In, $^{161}$Tb and $^{177}$Lu.

In one embodiment of the present invention is the linker a chelating linker.

A further aspect of the present invention relates to DNA molecule comprising a region encoding the variable heavy chain and/or the variable light chain of an antibody of the present invention.

Another aspect of the present invention relates to an immunoconjugate comprising the monoclonal antibody of the present invention or a functional fragment thereof.

A further aspect of the present invention relates to a host cell carrying one or more vectors comprising a DNA molecule of the present invention.

In one embodiment of the present invention is the cell a hybridoma cell line.

A further aspect of the present invention relates to a pharmaceutical composition comprising, as the active ingredient, one or more monoclonal antibodies that binds to CD146 according to the invention, and a pharmaceutically acceptable carrier.

Yet another aspect of the present invention relates to a pharmaceutical composition of the present invention for use in the treatment of cancer.

Another aspect of the present invention relates to a method for producing an antibody as described in the present invention, comprising transfecting a mammalian host cell with one or more vectors of the present invention, culturing the host cell and recovering and purifying the antibody molecule.

A further aspect of the present invention relates to a method for treating a patient suffering from a cancer comprising administering to said patient an effective amount of a pharmaceutical composition of the invention.

Another aspect of the present invention relates to the use of the monoclonal antibody of the present invention or the radioimmunoconjugate of the present invention, for the treatment of cancer. In one embodiment of treating cancer, unlabelled antibody is administered prior to radioimmunotherapy (RIT) or antibody drug conjugate (ADC) to reduce normal tissue binding of the active (RIT/ADC) drug.

Another aspect of the present invention relates to a method of diagnosing of cancer in a subject, comprising; contacting a sample from the subject with the isolated monoclonal antibody of the present invention or functional fragment thereof, and detecting binding of the isolated monoclonal antibody or functional fragment thereof to the sample, wherein a significant increase in binding of the isolated monoclonal antibody or functional fragment thereof to the sample as compared to binding of the isolated human monoclonal antibody or functional fragment thereof to a control sample diagnoses the subject with cancer.

A further aspect of the present invention relates to a kit for the production of the radioimmunoconjugate of the present invention comprising two or more vials, wherein one vial contains a conjugate comprising a chelator linked to an antibody according to anyone of the present invention; and a second vial comprising a radionuclide.

An additional aspect of the present invention was the unexpected observation that radioimmunotherapy using radiolabeled OI-3 could cause a subsequent upregulation of the binding of antibody targeting co-expressed antigen, e.g., Her-2. It is has been reported that external beam radiation can up regulate antigen expression in cancer cells (e.g. Voutsas et al., 2013). However, data from experimental radioimmunotherapy has so far indicated reduced expression from this modality (Orbom et al., 2013; Elgstrom et al., 2012) or a mixed response with CEA being reduced, keratin and epithelial membrane antigen being unchanged and TAG-72 being elevated at resurgent tumors 6 weeks after therapy (Esteban et al., 1991). In another study, however, (Schlom et al., 1990) it was reported no difference in TAG-72 between treated and non-treated tumors. Thus, in the field of radioimmunotherapy there is little or no data supporting antigen upregulation in solid tumors.

The upregulation of co-expressed antigens observed for the present invention suggest that combination therapy or induction therapy using OI-3 or derivatives thereof including radioimmunoconjugates can be used in combination with targeted therapy against co-expressed antigens.

FIG. 1 Flow cytometry with OI-3 on human osteosarcoma cell line Saos-2, using isotype specific anti-murine secondary antibodies.

Figure 2:
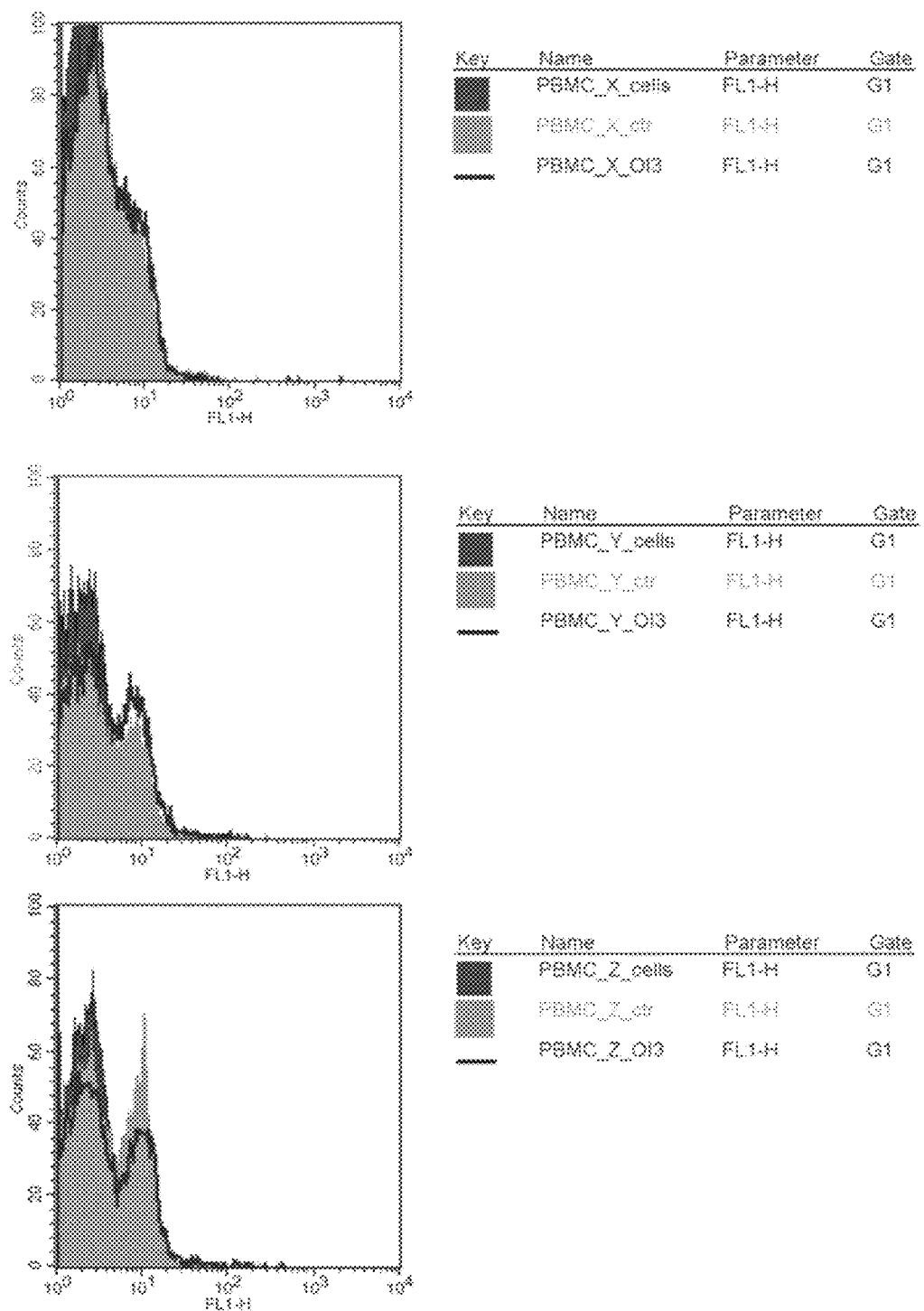

FIG. 2 Flow analysis of Peripheral Blood Mononuclear Cells (PBMC) from three different individuals (named X, Y and Z). Cells: Background/autofluorescence of unlabelled cells. Ctr: only secondary antibody. Secondary antibody alone gives some background staining. OI-3 is negative; does not bind PBMC.

Figure 3:
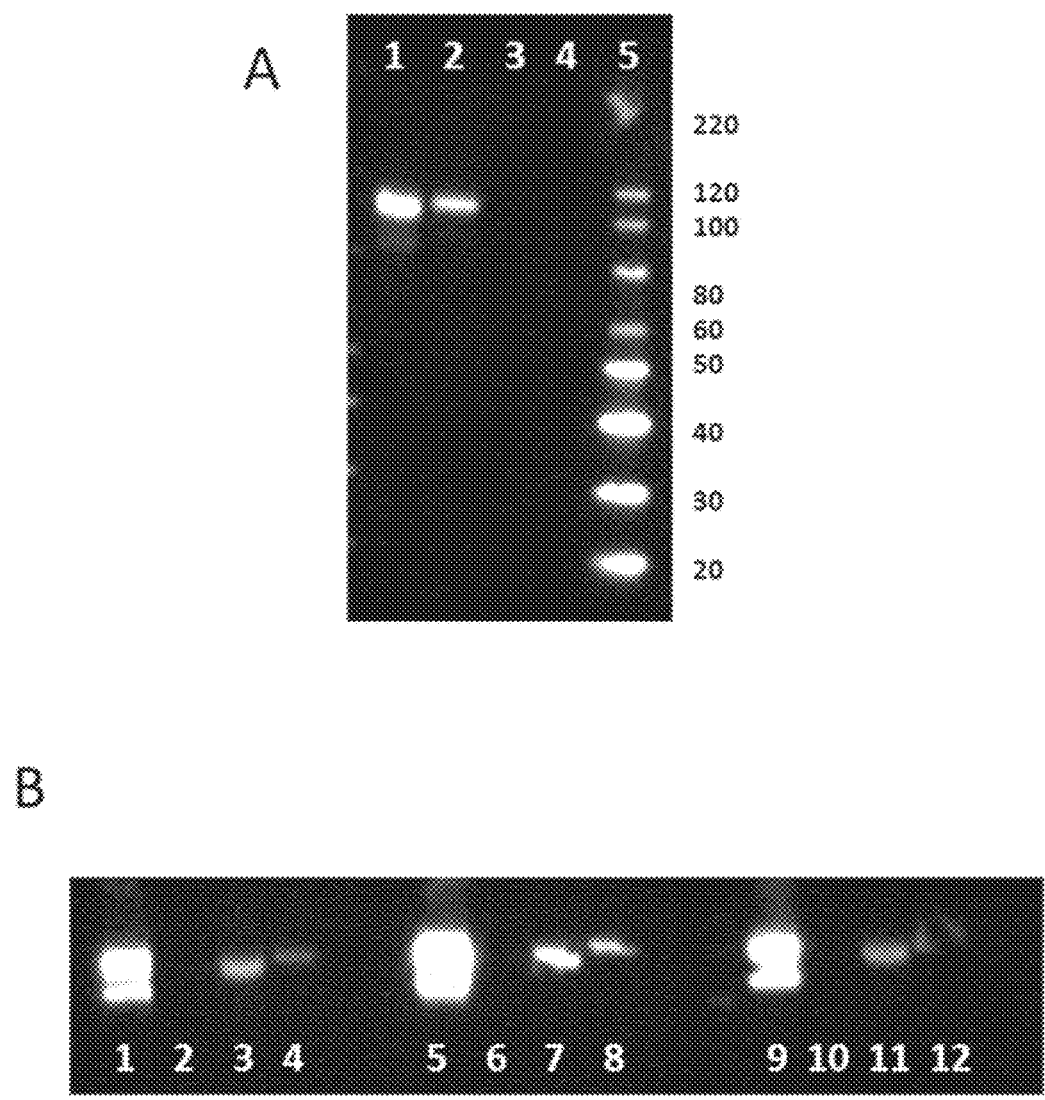

FIG. 3 A: Western blot with OI-3 as primary antibody. Lane 1: OHS lysate, lane 2: A375 lysate, lane 3: SKOV-3 lysate, lane 4: empty lane: lane 5: MagicMark Protein Standard. B: Western blot with the following primary antibodies: OI-3 (1-4), P1H12 (lane 5-8) and EPR3208 (lane 9-12). Lysates on each membrane: CD146 overexpressing cells, vector transfected lysate control (2, 6, 10), MelJRpost3.3 (lane 3, 6, 11) and (OHS 4, 8, 12). No bands are visible for the control lysate for any of the primary antibodies.

Figure 4:
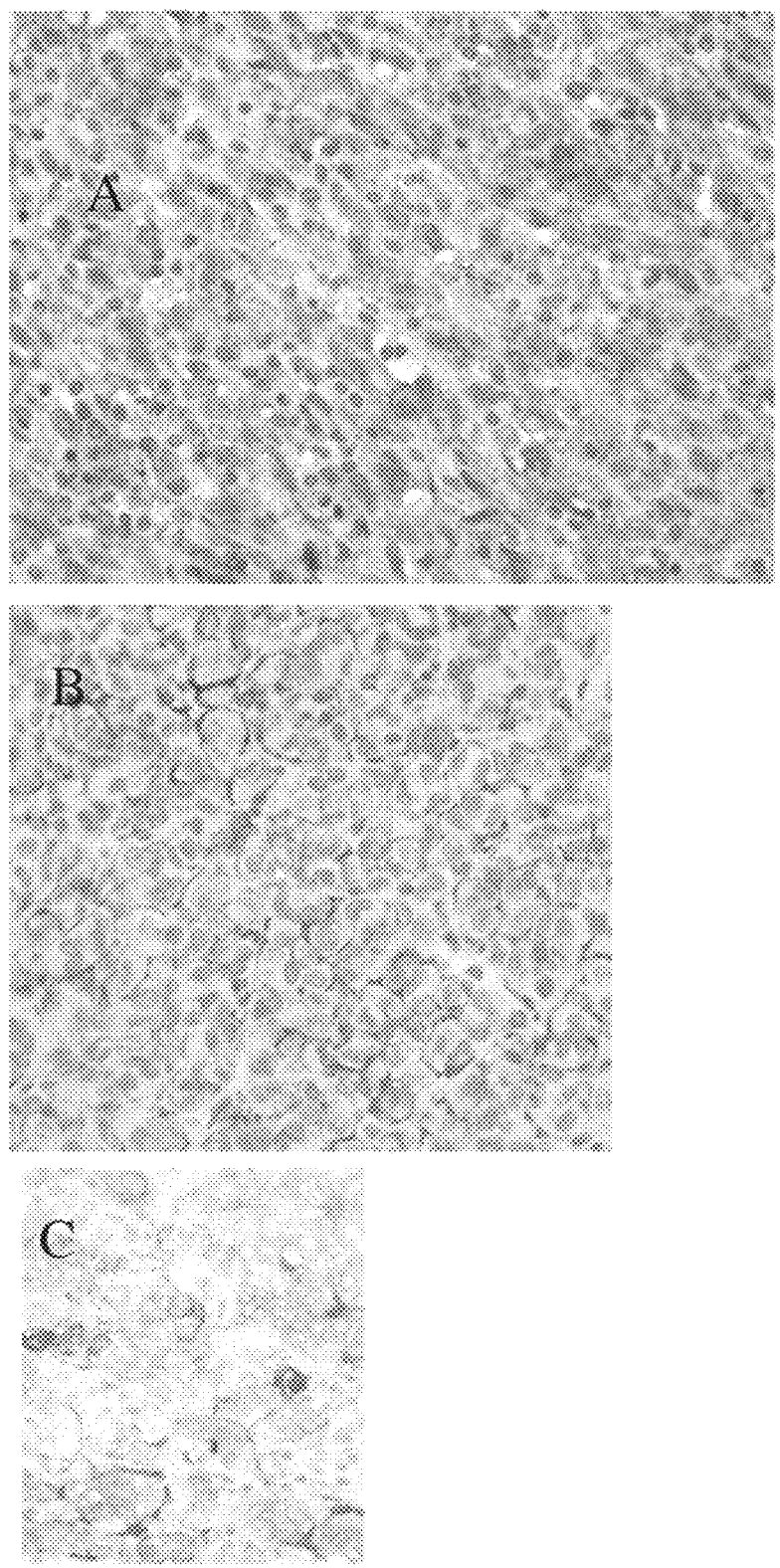

FIG. 4 Immunohistochemistry analysis of OI-3 conjugated to HRP. Positive staining to paraffin section of human melanoma cells (A), to paraffin section of lung tumors in SCID mice with metastatic MelJRpost3.3 (B), and to frozen section of the lung tumors from the murine model (C).

Figure 5:
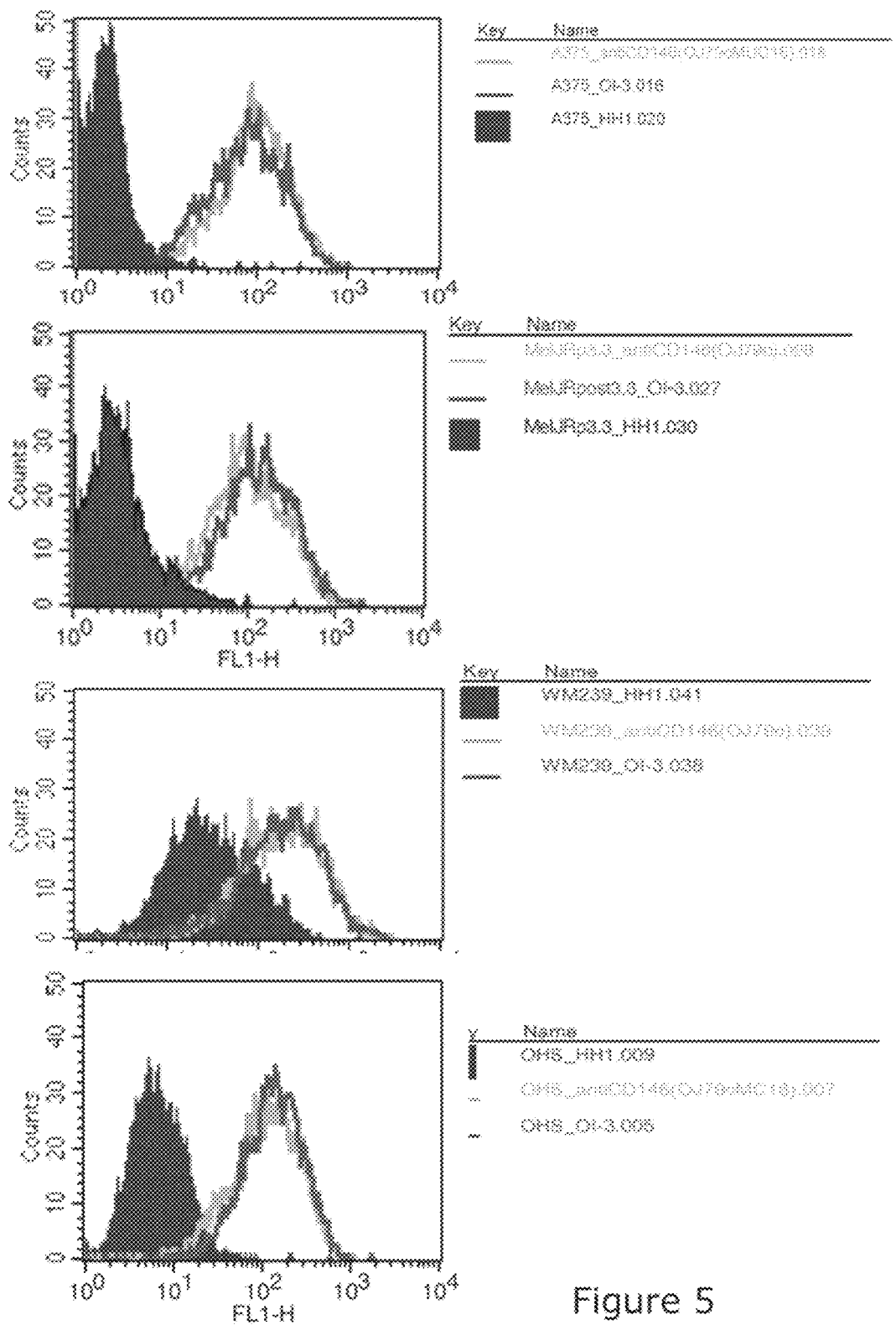
Figure 5:
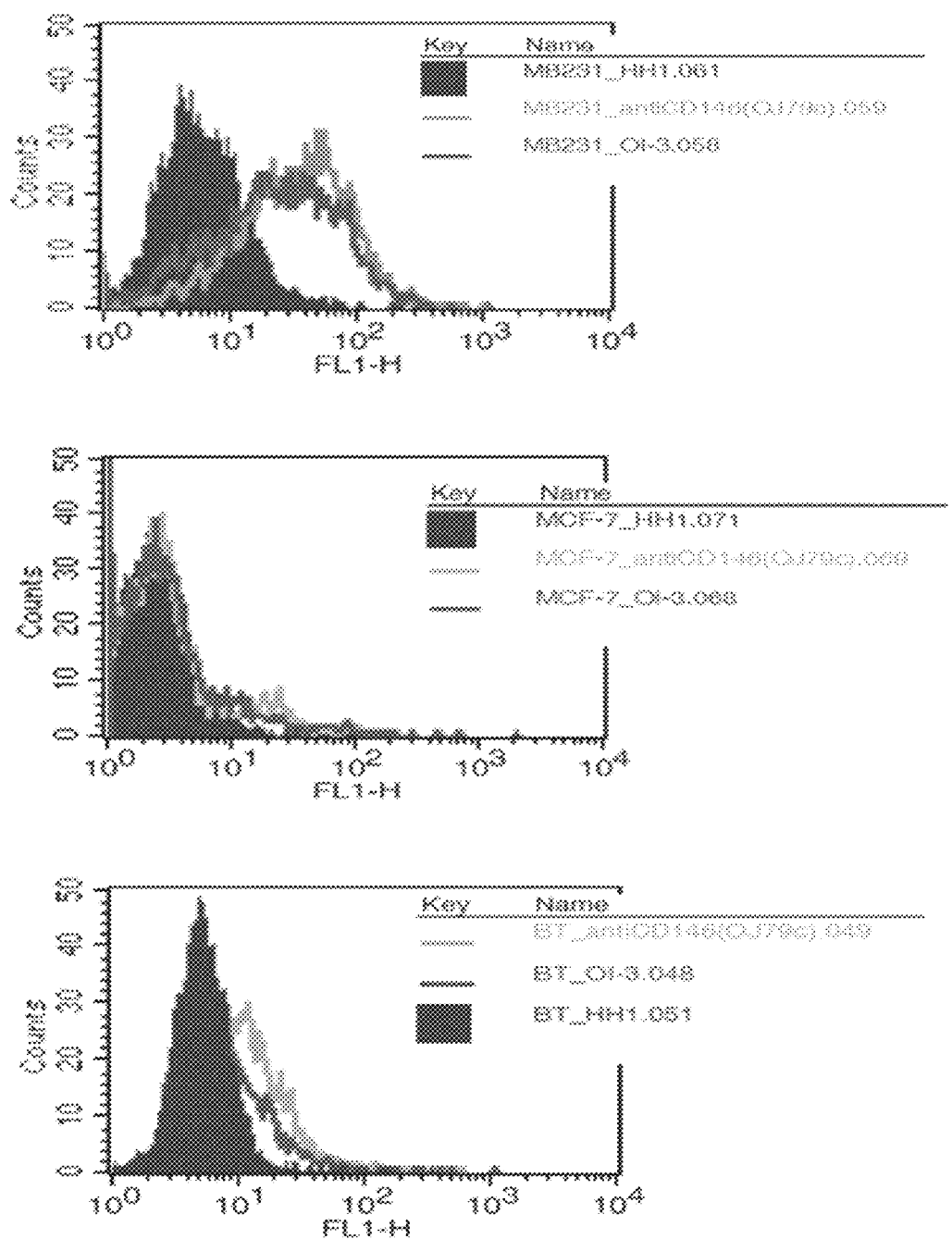

FIG. 5 Flow cytometry histogram of parallel samples of melanoma (A375, MelJRpost3.3, WM239), osteosarcoma (OHS), and breast cancer (MDA-MB-231, MCF-7 and BT-474) cell lines stained with OI-3 and a commercial murine CD146 antibody, and a non-binding IgG1 antibody control; B-cell specific marker; anti CD37 (HH1). Secondary antibody: Anti-murine IgG FITC in all applications.

Figure 6:
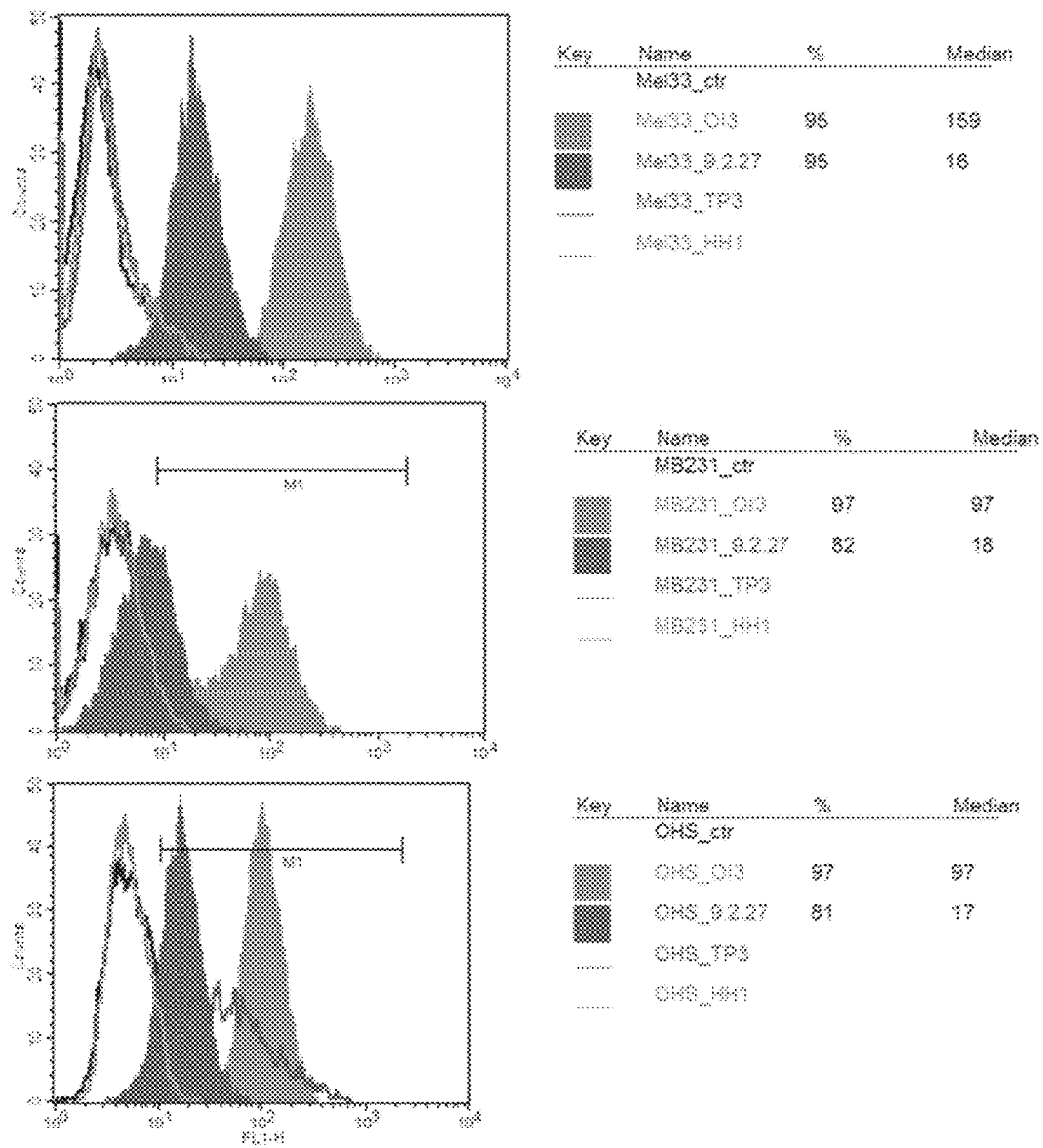

FIG. 6 Flow analysis of OI-3, 9.2.27, TP3 and HH1 stained MelJRpost3.3, MDA-MB-231 and OHS cells. Ctr: only secondary antibody. Background staining is excluded by definition of M1 for statistics. For M1; percentage of cells stained (%) and median linear value.

Figure 7:
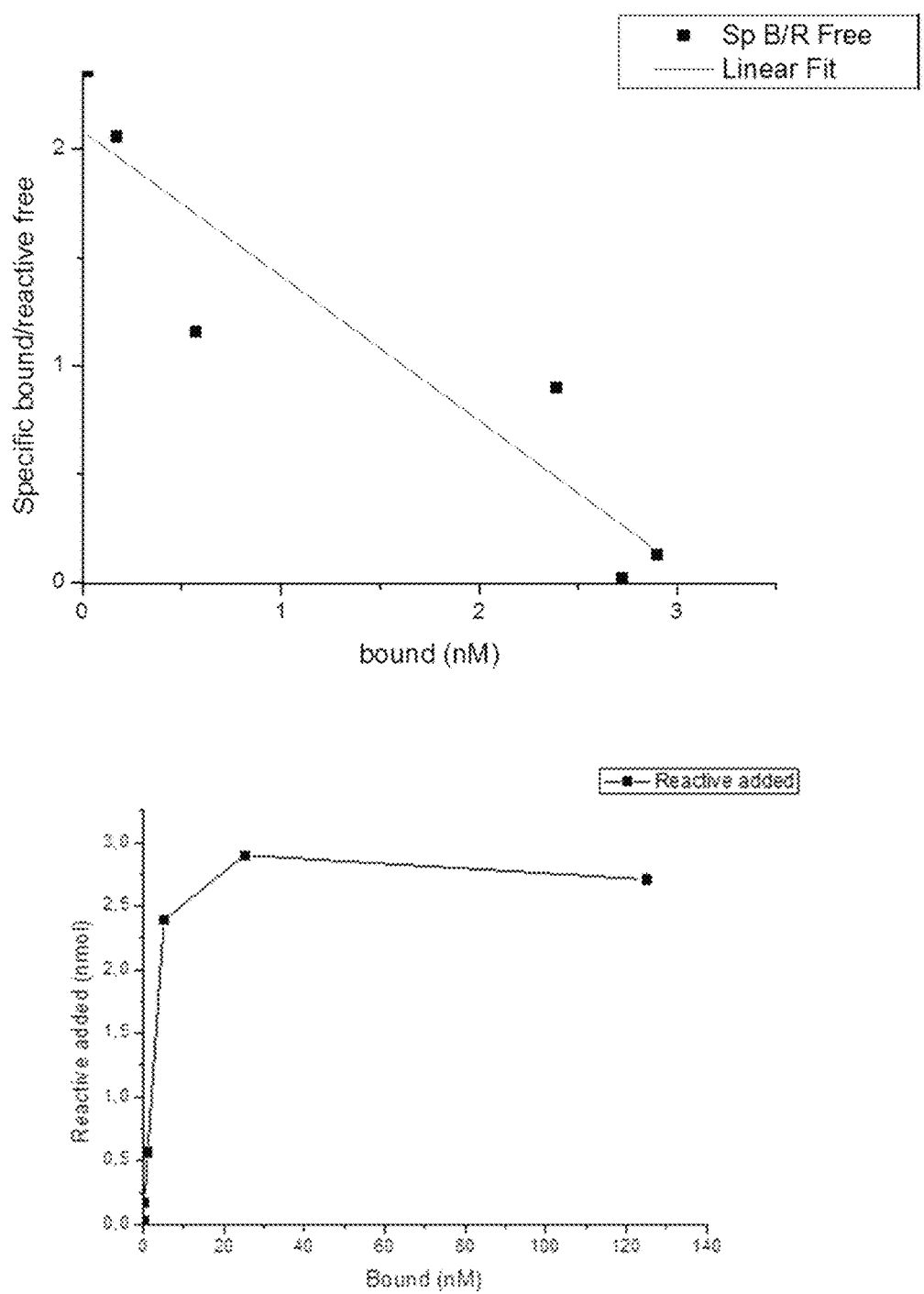

FIG. 7 Scathard plot (upper) and binding plot (lower).

Figure 8:
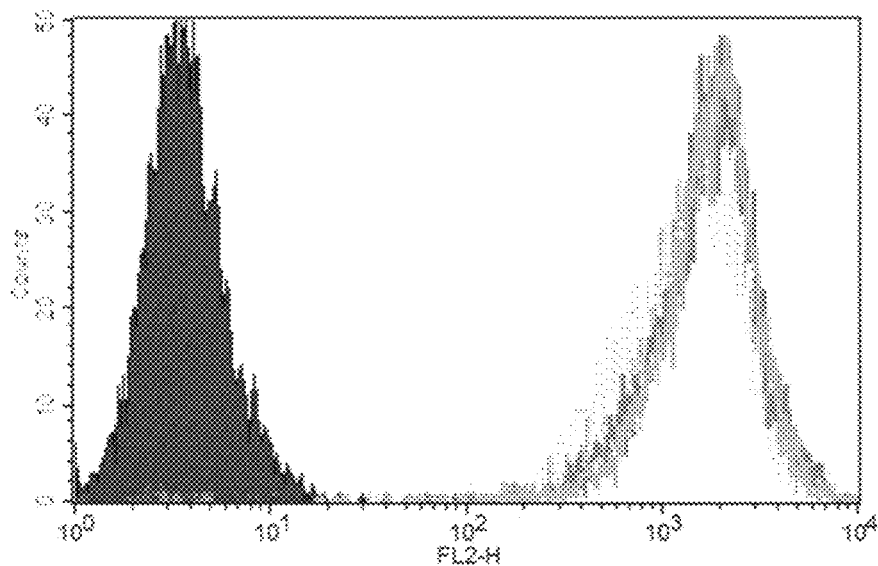

FIG. 8 Flow cytometry plots of chimeric versions of OI-3.

Figure 9:
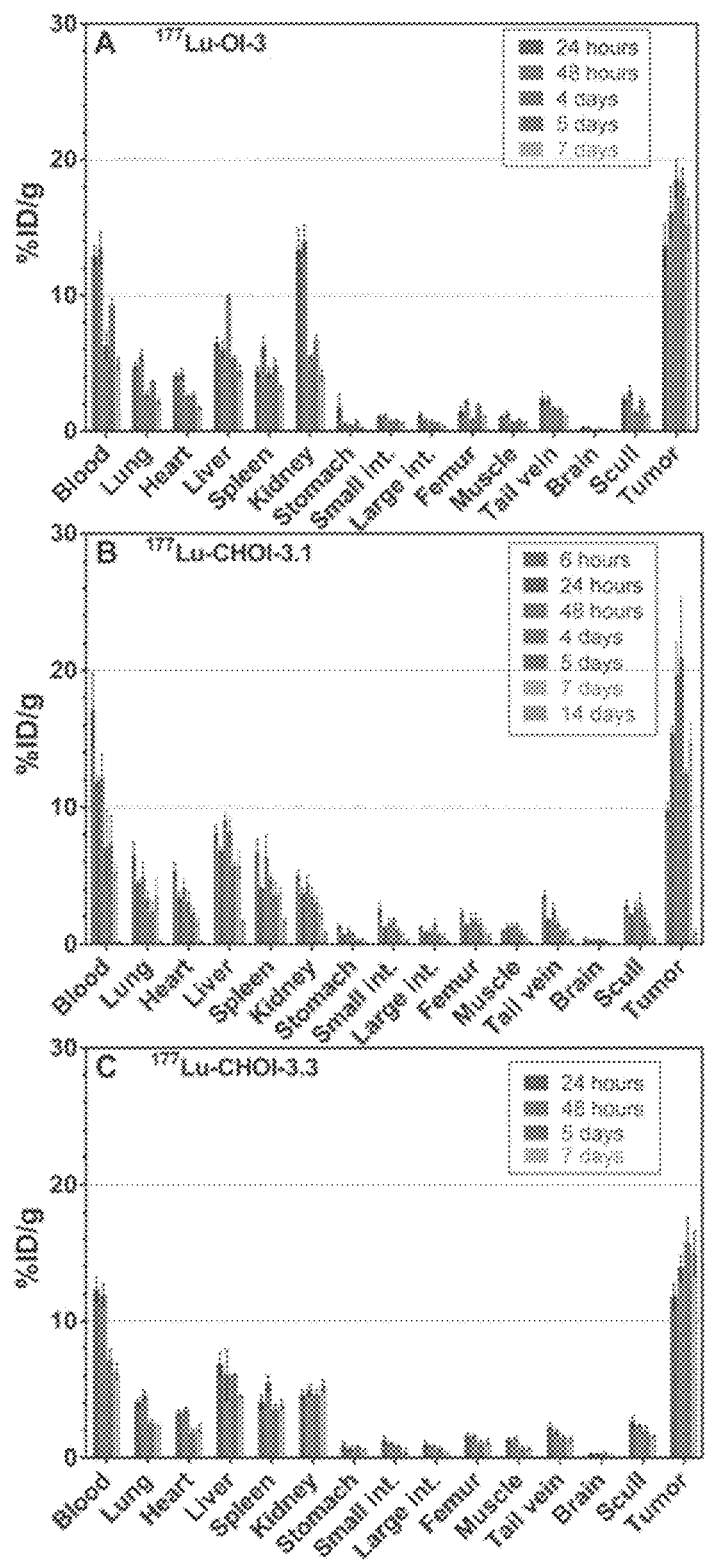

FIG. 9 Biodistribution (% ID/g) of $^{177}$Lu-OI-3 (A), $^{177}$Lu-CHOI-3.1 (B) and $^{177}$Lu-CHOI-3.3 (C) in female nude mice with OHS tumor xenografts. Error bars correspond to standard error.

Figure 10:
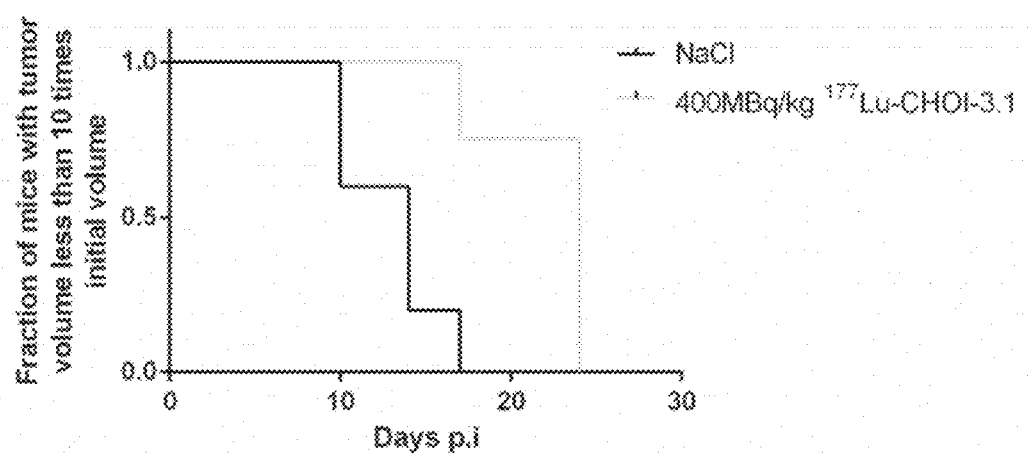

FIG. 10 Fraction of mice with tumor volume less than 10 times volume at treatment start as a function of time. A comparison of the curves with a Log-rank (Mantel-Cox) test.

DETAILED DESCRIPTION OF THE INVENTION

The present inventors have tested a new monoclonal antibody OI-3 against CD146 that has a relevant Ka and a promising signals in flow cytometry.

In the work by Zhang et al (2008) a panel of monoclonal antibodies against CD146 was generated using purified CD146 extract as immunization agent. These antibodies varied strongly in their binding properties regarding binding to living cells and frozen tissue sections or paraffin embedded sections. When grouped into two groups, one group could bind to living cells and frozen tissue sections and the other group stained paraffin embedded sections. It was suggested that the latter group recognized epitopes not exposed on protein surface of living cells thus causing a lack of reactivity in flow cytometry.

With the work by Zhang et al (2008) in mind it was unexpected to find that OI-3 binds to living cells, frozen tissue sections and paraffin-embedded sections altogether. Thus it would fit into the classification system they used. This indicates that Oi-3 targets a versatile epitope on CD146.

This could possibly be the effect of using whole osteosarcoma cells instead of cell extracts for the immunization leading to the OI-3 as the availability of epitopes may vary for different antigen presenting forms.

Thus it is indicated that the OI-3 antibody could represent a substantial improvement in the targeting of CD146 expressing malignant cells with monoclonal antibody.

The present invention provides a novel monoclonal antibody, OI-3, which targets the cancer associated CD146 antigen. The OI-3 binds well to cell lines from several different cancer forms as indicated by binding to osteosarcoma, melanoma and breast cancer cell lines.

It is presented here that pre-treatment with other CD146 antibodies could to some degree block the binding of radiolabeled OI-3 on antigen positive cells, but would not cause a complete blocking of the binding while pre-treatment with OI-3 would cause a complete blocking. This observation is consistent with the hypothesis that steric hindrance caused by the significant amount of antibody bound to various epitopes at the same antigen, in general is making the antigen, including the OI-3 related epitope, less accessible to macromolecules.

It is also shown that OI-3 antibody is well suited for radiolabeling using modification of tyrosine or lysine side chains.

The invention covers the amino acid structures of OI-3 in general, and in particular the amino acid structures of the antigen combining sites.

Within the scope of the invention is the use of OI-3 to prepare murine, chimeric or humanized antibodies, or versions based on framework from other mammals including dog, with the same or significantly similar epitope targeting as well as the use of such for diagnosis, imaging or therapy against CD146 expressing cells.

The new antibody, the OI-3, is a monoclonal antibody of subclass IgG1. It was generated by standard hybridoma method, i.e., by immunizing mice with tumor cells and cell extracts and later on harvest spleen cell and fuse these with murine myeloma cells.

The main difference from the generation of other anti CD146 antibodies was the use of osteosarcoma cells for immunization instead of melanoma cells or melanoma cell extracts. Cloning and recloning were performed to obtain a productive clone yielding the OI-3 antibody.

Data from various assays using radiolabeled antibodies or flow cytometryon a panel of CD146 positive and negative cells were consistent with CD146 specificity. Immunoprecipitation followed by SDS page with coomassie blue staining of the gel indicated precipitation of an antigen with same size as that precipitated with the CD146 binding antibody.

Flow data indicated a binding to melanoma cells and breast cancer cells with the OI-3. With osteosarcoma cells three cells lines were positive for OI-3. This indicate a significant potential as antitumor targeting agent for OI-3

With a mixture of monoclonal and polyclonal antibodies against CD146 was used or pre- and co-treatment, the blocking of radiolabeled OI-3 was significant but incomplete indicating that OI-3 binds to a substantially different epitope on the antigen.

This observation is consistent with the hypothesis that steric hindrance caused by the significant amount of antibody bound to various epitopes at the same antigen, in general is making the antigen, including the OI-3 related epitope, less accessible to macromolecules.

Monoclonal OI-3 Antibody and Variations Hereof

One aspect of the present invention relates to an antibody molecule that binds to human CD146 and that is a monoclonal antibody that is defined by a variable heavy chain comprising the amino acid sequence shown in SEQ ID NO: 3; and a variable light chain comprising the amino acid sequence shown in SEQ ID NO: 4, or a monoclonal antibody recognizing the same epitope of human CD146 as the antibody defined above or recognizing an epitope that is close to or overlaps with said epitope, or a monoclonal antibody that share at least 80% sequence identity with the antibodies defined above.

One embodiment of the present invention relates to an antibody molecule of the present invention that is defined by a variable heavy chain comprising the amino acid sequence shown in SEQ ID NO: 3; a variable light chain comprising the amino acid sequence shown in SEQ ID NO: 4, and constant heavy and light chains that are of mammalian origin.

Another embodiment of the present invention relates to an antibody molecule of the present invention, wherein the constant heavy chain is selected from the group consisting of IgG1, IgG2, IgG3 and IgG4 chain, and the constant light chain is a kappa or a lambda chain.

A further embodiment of the present invention relates to an antibody molecule of the present invention, wherein said constant heavy chain comprises the amino acid sequence shown in SEQ ID NO: 6, and/or SEQ ID NO: 7 and wherein said constant light chain comprises the amino acid sequence shown in SEQ ID NO: 5.

In a preferred embodiment of the present invention is the antibody the monoclonal antibody OI-3.

Within the scope of this invention is epitope-recognizing peptides, antibody fragments like Fab and F(ab)2, Single-chain variable fragments like diabodies, or multivalent bodies either murine or recombinant with or without protein sequences from other mammalian or non-mammalian species including products produced by expression in hybridomas, e-coli, or other expression systems.

For some purposes the OI-3 could be enzymatically or chemically digested to yield antibody fragments. Such fragments are functional fragments of OI-3.

Chimeric and Humanized Antibodies Derived from OI-3

Because of the favourable binding properties of the OI-3 antibody, it is suitable to generate chimeric and/or human versions of OI-3 which could be appropriate for human in vivo use.

The immunoglobulin heavy chain (IgH) is the large polypeptide subunit of an antibody (immunoglobulin).

A typical antibody is composed of two immunoglobulin (Ig) heavy chains and two Ig light chains.

Several different types of heavy chain exist that define the class or isotype of an antibody.

These heavy chain types vary between different animals.

The immunoglobulin light chain is the small polypeptide subunit of an antibody (immunoglobulin).

There are two types of light chain in humans (as in other mammals), kappa (κ) chain, encoded by the immunoglobulin kappa locus on chromosome 2 and the lambda (λ) chain, encoded by the immunoglobulin lambda locus on chromosome 22.

Antibodies are produced by B lymphocytes, each expressing only one class of light chain.

Once set, light chain class remains fixed for the life of the B lymphocyte.

In a healthy individual, the total kappa to lambda ratio is roughly 2:1 in serum (measuring intact whole antibodies) or 1:1.5 if measuring free light chains, with a highly divergent ratio indicative of neoplasm.

The exact normal ratio of kappa to lambda ranges from 0.26 to 1.65.

Both the kappa and the lambda chains can increase proportionately, maintaining a normal ratio.

Both variable and constant chains in a chimeric or humanized antibody derived from the mouse monoclonal antibody OI-3 can differ from known sequences.

Examples of such variations are clear from the present disclosure and include selection of constant chains, genetic variation of variable chains and variations of the Fc domain in order to modulate of effector functions.

The present inventors have genetically engineered chimeric, humanized antibodies derived from the mouse monoclonal antibody OI-3.

These antibodies show a promising effect in the search for optimal treatment several types of cancer.

These effects are shown in the experiments of the present disclosure.

Thus, one aspect of the present invention relates to an antibody molecule that binds to human CD146 and that is derived from a monoclonal antibody that is defined by a variable heavy chain comprising the amino acid sequence shown in SEQ ID NO: 3; and a variable light chain comprising the amino acid sequence shown in SEQ ID NO: 4, or from a non-human antibody recognizing the same epitope of human CD146 as the antibody defined above or recognizing an epitope that is close to or overlaps with said epitope; wherein said antibody molecule is a chimeric or a humanized antibody.

In one embodiment of the present invention is the antibody molecule of the present invention a chimeric antibody defined by a variable heavy chain comprising the amino acid sequence shown in SEQ ID NO: 3; a variable light chain comprising the amino acid sequence shown in SEQ ID NO: 4, and constant heavy and light chains that are of human origin.

In another embodiment of the present invention is the constant heavy chain is selected from the group consisting of IgG1, IgG2, IgG3 and IgG4 chain, and the constant light chain is a kappa or a lambda chain.

In a further embodiment of the present invention is comprises the constant heavy chain the amino acid sequence shown in SEQ ID NO: 6, and/or SEQ ID NO: 7 and wherein said constant light chain ii) comprises the amino acid sequence shown in SEQ ID NO: 5.

Sequence Identity

As commonly defined "identity" is here defined as sequence identity between genes or proteins at the nucleotide or amino acid level, respectively.

Thus, in the present context "sequence identity" is a measure of identity between proteins at the amino acid level and a measure of identity between nucleic acids at nucleotide level.

The protein sequence identity may be determined by comparing the amino acid sequence in a given position in each sequence when the sequences are aligned.

Similarly, the nucleic acid sequence identity may be determined by comparing the nucleotide sequence in a given position in each sequence when the sequences are aligned.

To determine the percentage identity of two nucleic acid sequences or of two amino acids, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared.

When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

One may manually align the sequences and count the number of identical nucleic acids or amino acids. Alternatively, alignment of two sequences for the determination of percent identity may be accomplished using a mathematical algorithm. Such an algorithm is incorporated into the NBLAST and XBLAST programs. BLAST nucleotide searches may be performed with the NBLAST program, score=100, wordlength=12, to obtain nucleotide sequences homologous to a nucleic acid molecules of the invention. BLAST protein searches may be performed with the XBLAST program, score=50, wordlength=3 to obtain amino acid sequences homologous to a protein molecule of the invention.

To obtain gapped alignments for comparison purposes, Gapped BLAST may be utilised. Alternatively, PSI-Blast may be used to perform an iterated search which detects distant relationships between molecules. When utilising the NBLAST, XBLAST, and Gapped BLAST programs, the default parameters of the respective programs may be used. See http://www.ncbi.nlm.nih.gov. Alternatively, sequence identity may be calculated after the sequences have been aligned e.g. by the BLAST program in the EMBL database (www.ncbi.nlm.gov/cgi-bin/BLAST).

Generally, the default settings with respect to e.g. "scoring matrix" and "gap penalty" may be used for alignment. In the context of the present invention, the BLASTN and PSI BLAST default settings may be advantageous.

The percent identity between two sequences may be determined using techniques similar to those described above, with or without allowing gaps. In calculating percent identity, only exact matches are counted.

An embodiment the invention relates to an isolated nucleic acid comprising a nucleic acid sequence sharing 80% sequence identity with the OI-3 antibody VH sequence (SEQ ID NO: 1) and/or VL sequence (SEQ ID NO: 2).

An embodiment the invention relates to an isolated nucleic acid comprising a nucleic acid sequence with the OI-3 antibody VH sequence (SEQ ID NO: 1) and/or VL sequence (SEQ ID NO: 2).

In another embodiment of the invention the isolated nucleic acid comprises a nucleic acid sequence sharing at least 90% sequence identity with the OI-3 antibody VH sequence (SEQ ID NO: 1) and/or VL sequence (SEQ ID NO: 2), such as 90% identity, 91% identity, 92% identity, 93% identity, 94% identity, 95% identity, 96% identity, 97% identity, 98% identity, or 99% identity.

Another embodiment of the invention relates to an antibody comprising a polypeptide sequence sharing 80% sequence identity with the OI-3 antibody VH sequence (SEQ ID NO: 3) and/or VL sequence (SEQ ID NO: 4).

Another embodiment of the invention relates to an antibody comprising a polypeptide sequence with the OI-3 antibody VH sequence (SEQ ID NO: 3) and/or VL sequence (SEQ ID NO: 4).

In another embodiment of the present invention, the antibody comprises a polypeptide sequence sharing at least 90% sequence identity with the OI-3 antibody VH sequence (SEQ ID NO: 3) and/or VL sequence (SEQ ID NO: 4), such as 90% identity, 91% identity, 92% identity, 93% identity, 94% identity, 95% identity, 96% identity, 97% identity, 98% identity, or 99% identity.

In a preferred embodiment of the present invention are these antibodies a murine, chimeric or humanized antibody derived from the monoclonal antibody OI-3.

Genetic Variation

Genetic variation is caused by variation in the order of bases in the nucleotides in genes. This variation cause mutations in the genes and subsequently in the proteins that such genes encode.

These mutations can be either sense or missense mutations or substitutions.

An embodiment of the present invention relates to the isolated nucleic acid sequence of the OI-3 monoclonal antibody VH chain (SEQ ID NO: 1) and/or VL chain (SEQ ID NO: 2) that comprises at least 50, such as 20, such as 10, such as 5, such as 4, such as 3, such as 2, such as 1 sense mutations.

Another embodiment of the present invention relates to the isolated nucleic acid sequence of the OI-3 monoclonal antibody VH chain (SEQ ID NO: 1) and/or VL chain (SEQ ID NO: 2) that comprises 0-50, such as 1-50, such as 0-20, such as 1-20, such as 0-10, such as 1-10, such as 0-5, such as 1-5, such as 3, such as 1 sense mutations.

A missense mutation (a type of non-synonymous mutation) is a point mutation in which a single nucleotide is changed, resulting in a codon that code for a different amino acid (mutations that change an amino acid to a stop codon are considered nonsense mutations, rather than missense mutations). A missense mutation can render the resulting protein non-functional.

However, not all missense mutations lead to appreciable protein changes. An amino acid may be replaced by an amino acid of very similar chemical properties, in which case, the protein may still function normally; this is termed a neutral, "quiet", or conservative mutation.

Alternatively, the amino acid substitution could occur in a region of the protein which does not significantly affect the protein secondary structure or function. When an amino acid may be encoded by more than one codon (so-called "degenerate coding") a mutation in a codon may not produce any change in translation; this would be a synonymous mutation (a form of silent mutation) and not a missense mutation.

An embodiment of the present invention relates to an antibody comprising a polypeptide sequence of the OI-3 monoclonal antibody VH chain (SEQ ID NO: 3) and/or VL chain (SEQ ID NO: 4) that comprises at least 50, such as 20, such as 10, such as 5, such as 4, such as 3, such as 2, such as 1 missense mutations.

An embodiment of the present invention relates to an antibody comprising a polypeptide sequence of the OI-3 monoclonal antibody VH chain (SEQ ID NO: 3) and/or VL chain (SEQ ID NO: 4) that comprises 0-50, such as 1-50, such as 0-20, such as 1-20, such as 0-10, such as 1-10, such as 0-5, such as 1-5, such as 3, such as 1 missense mutations.

A conservative substitution is a substitution of one amino acid with another with generally similar properties such that the overall functioning is likely not to be seriously affected.

In another embodiment of the present invention are the missense mutations conservative mutations or substitutions.

A further embodiment of the present invention relates to an isolated nucleic acid sequence or a polypeptide sequence with 80% sequence identity to the variable heavy chain (SEQ ID NO: 3) and/or variable light chain (SEQ ID NO: 4) sequences of OI-3, wherein the sequence variation is conservative substitutions.

In another embodiment of the present invention is the sequence identity 80% identity, such as 90% identity, 91% identity, 92% identity, 93% identity, 94% identity, 95% identity, 96% identity, 97% identity, 98% identity, or 99% identity and the sequence variation is conservative substitutions.

Functional fragments of the antibodies of the present invention comprise parts of the OI-3 antibody that are capable of generating an immune response similar to that of OI-3.

Such fragments can also be used in the methods of the present invention instead of the full length OI-3.

In order to improve the radiolabeling step it may be beneficial to introduce extra lysine into e.g., the Fc portion of the chimeric or humanized antibody of the present invention.

This could reduce the probability of attaching lysine binding chelators into the antigen combining sites at the antibody, thereby reducing the risk of compromising immunoreactivity during radiolabeling.

Methods for introducing lysine into e.g. the Fc portion of OI-3 is known in the art e.g. from Hemminki et al., 1995.

An embodiment of the present invention relates to the radioimmunoconjugate of the present invention which has been modified by 10 Lys in the Fc portion of OI-3, such as 8 Lys, such as 6 Lys, such as 5 Lys, such as 4 Lys, such as 3 Lys, such as 2 Lys, such as 1 Lys.

Other variations of the Fc portion of the antibodies of the present invention can be chosen in order to optimize or modulate one or more effector functions.

These modulations of effector functions are made e.g. to increase in antibody-dependent cell-mediated cytotoxicity (ADCC).

Such variations of the Fc portion are known in the art.

Thus, one aspect of the present invention relates to an antibody of the present invention that has one or more mutations in the Fc domain that modulate one or more effector functions.

Radioimmunoconjugates

One aspect of the present invention relates to a radioimmunoconjugate that binds human CD146 comprising an antibody of the present invention, a linker, and a radionuclide.

In one aspect of the present invention is the radionuclide selected from the group consisting of $^{211}At$, $^{213}Bi$, $^{212}Bi$, $^{212}Pb$, $^{225}Ac$, $^{227}Th$, $^{90}Y$, $^{186}Re$, $^{188}Re$, $^{199}Au$, $^{194}Ir$, $^{166}Ho$, $^{159}Gd$, $^{153}Sm$, $^{149}Pm$, $^{142}Pr$, $^{111}Ag$, $^{109}Pd$, $^{77}As$, $^{67}Cu$, $^{47}Sc$, $^{230}$U, $^{226}$Th, $^{223}$Ra, $^{224}$Ra, $^{225}$Ra, $^{131}$I, $^{18}$F, $^{64}$Cu, $^{67}$Ga, $^{99m}$Tc, $^{123}$I, $^{124}$I, $^{125}$I, $^{131}$I, $^{111}$In, $^{161}$Tb and $^{177}$Lu.

In an embodiment of the present invention the linker is a chelating linker.

In another embodiment of the present invention is the radionuclide selected from the group consisting of $^{177}$Lu, $^{225}$Ac, $^{227}$Th and $^{90}$Y.

In another embodiment of the present invention the radionuclide is $^{177}$Lu.

In yet another embodiment the radionuclide is another beta-emitter or an alpha-emitter.

The radionuclide may be attached to the antibody by first reacting with a bifunctional chelator, e.g., p-SCN-bn-DOTA (Macrocyclics, Tx, USA), with the antibody, followed by purification to remove unconjugated chelator, and then reaction of the chelator antibody conjugate with the radionuclide, followed by purification to remove any unconjugated radionuclide.

Alternatively, the chelator and the radionuclide can be combined firstly and subsequently conjugated to the antibody.

Chelating linkers like, e.g., p-SCN-bn-DOTA, can be used for conjugating other metal radionuclides to OI-3 derived antibodies in similar fashion to that described for $^{177}$Lu.

Any type of linker with sufficient complexing ability and a functional group allowing direct or indirect conjugation to a protein or a peptide could be used. Examples of such linkers are described in the literature (e.g. Brechbiel, 2008; Liu, 2008). Some useful examples are bifunctional cyclic chelators like p-SCN-bn-DOTA, DOTA-NHS-ester; bifunctional linear chelators like p-SCN-Bn-DTPA and CHX-A"-DTPA.

The radionuclides in the present invention will preferably be conjugated to a targeting molecule by using bifunctional chelators.

These could be cyclic, linear or branched chelators. Particular reference may be made to the polyaminopolyacid chelators which comprise a linear, cyclic or branched polyazaalkane backbone with acidic (e.g. carboxyalkyl) groups attached at backbone nitrogens.

Examples of suitable chelators include DOTA derivatives such as p-isothiocyanatobenzyl-1,4,7,10-tetraazacyclododecane-1,4,7,10-tetraacetic acid (p-SCN-Bz-DOTA) and DTPA derivatives such as p-isothiocyanatobenzyl-diethylenetriaminepentaacetic acid (p-SCN-Bz-DTPA), the first being cyclic chelators, the latter linear chelators.

Metallation of the complexing moiety may be performed before or after conjugation of the complexing moiety to the targeting moiety.

The radiolabeling procedure will in general be more convenient in terms of time used etc if the chelator is conjugated to the antibody before the radiolabeling takes place.

The principles of preparing radiolabeled conjugates using chelators attached to antibodies are described broader in e.g. Liu, 2008.

Thus, OI-3 derived murine, chimeric or humanized antibodies can be used to prepare radioimmunoconjugates with differences in radiation properties and effective half-lives.

For example anti-CD146 radioimmunoconjugate consisting of a murine, chimeric or humanized antibody derived from the monoclonal antibody OI-3 according to the present invention, a chelating linker and a beta or alpha emitting radionuclide including, but not limited to $^{211}$At, $^{213}$Bi, $^{212}$Bi, $^{212}$Pb, $^{225}$Ac, $^{227}$Th, $^{90}$Y, $^{186}$Re, $^{188}$Re, $^{199}$Au, $^{194}$Ir, $^{166}$Ho, $^{159}$Gd, $^{153}$Sm, $^{149}$Pm, $^{142}$Pr, $^{111}$Ag, $^{109}$Pd, $^{77}$As, $^{67}$Cu, $^{47}$Sc, $^{230}$U, $^{226}$Th, $^{223}$Ra, $^{224}$Ra, $^{225}$Ra, $^{131}$I, $^{18}$F, $^{64}$Cu, $^{67}$Ga, $^{99m}$Tc, $^{123}$I, $^{124}$I, $^{125}$I, $^{131}$I, $^{111}$In, $^{161}$Tb and $^{177}$Lu can be prepared and used for preparing pharmaceutical preparations and used in therapeutic applications.

The OI-3 could be radiolabeled via tyrosine reactive as well as lysine reactive reagents, while retaining a relevant immunoreactivity, indicating suitability for use as a conjugate, i.e., radioimmunoconjugate, drug-antibody conjugate or toxin-antibody conjugate. Also nanoparticle or microparticle conjugates, including liposomal conjugates, could be made with OI-3 or derivatives of this.

Nano- or microparticle conjugates can obtain a high local retention of product in the affected cavity.

Thus relates one embodiment of the present invention to a nano- or microparticle comprising the monoclonal antibody of the present invention, radiolabelled or cold.

Nucleic Acid Molecules

The humanization processes or artificial generation of murine variations of OI-3 takes advantage of the fact that production of monoclonal antibodies can be accomplished using recombinant DNA to create constructs capable of expression in mammalian cell culture.

That is, gene segments capable of producing antibodies are isolated and cloned into cells that can be grown in a tank such that antibody proteins produced from the DNA of the cloned genes can be harvested en masse.

The step involving recombinant DNA provides an intervention point that can be readily exploited to alter the protein sequence of the expressed antibody.

The alterations to antibody structure that are achieved in the humanization process are therefore all effectuated through techniques at the DNA level.

Thus, an aspect of the present invention relates to a DNA molecule encoding the murine, humanized or chimeric antibodies of the present invention.

In one embodiment of the present invention encodes the DNA molecule a region encoding the variable heavy chain of a murine, humanized or chimeric antibody of the present invention.

In another embodiment of the present invention is this variable heavy chain encoding region fused to a region encoding a constant heavy chain of human origin.

Such human constant heavy chain can be selected from the group consisting of IgG1, IgG2, IgG3 and IgG4.

The human constant heavy chain can also be IgE or IgM.

In a further embodiment of the present invention comprises the human constant heavy chain one or more substitutions in the Fc region.

Another embodiment of the present invention relates to a DNA molecule comprising a region encoding the variable light chain of the chimeric or humanized antibody of the present invention.

Such variable light chain encoding region may be fused to a region encoding a constant light chain of human origin.

The constant light chain may be a kappa or a lambda chain.

In one embodiment of the present invention is the IgG1 kappa light chain encoded by a sequence shown in SEQ ID NO:5.

In another embodiment of the present invention is the IgG1 kappa heavy chain encoded by a sequence shown in SEQ ID NO:6.

In another embodiment of the present invention is the IgG3 kappa heavy chain encoded by a sequence shown in SEQ ID NO:7.

The DNA molecules can be constructed and optimized for expression in a target cell.

An expression vector, otherwise known as an expression construct, is generally a plasmid that is used to introduce a specific gene (in the present context the DNA molecule of the present invention) into a target cell.

Once the expression vector is inside the cell, the protein that is encoded by the gene is produced by the cellular-transcription and translation machinery ribosomal complexes.

The plasmid is frequently engineered to contain regulatory sequences that act as enhancer and promoter regions and lead to efficient transcription of the gene carried on the expression vector.

The goal of a well-designed expression vector is the production of large amounts of stable messenger RNA, and therefore proteins.

Expression vectors are basic tools for biotechnology and the production of proteins such as insulin that are important for medical treatments of specific diseases like diabetes.

After expression of the gene product, the purification of the protein is required; but since the vector is introduced to a host cell, the protein of interest should be purified from the proteins of the host cell.

Therefore, to make the purification process easy, the cloned gene should have a tag. This tag could be histidine (His) tag or any other marker peptide.

Thus, an aspect of the present invention therefore relates to an expression vector comprising a DNA molecule as described above.

The OI-3 antibody antigen binding sequences may also be expressed in various vectors for the production of fusion proteins or fragments.

Immunoconjugate

An immunotoxin is a human-made protein that consists of a targeting portion linked to a toxin. When the protein binds to that cell, it is taken in through endocytosis, and the toxin kills the cell.

They are usually used for the treatment of some kinds of cancer and a few viral infections.

These proteins are usually made of a modified antibody or antibody fragment, attached to a fragment of a toxin.

The targeting portion is composed of the Fv portion of an antibody that targets a specific cell type.

The toxin is usually a cytotoxic protein derived from a bacterial or plant protein, from which the natural binding domain has been removed so that the Fv directs the toxin to the antigen on the target cell.

The immunotoxin works by the antibody (or other targeting moiety) binding to an antigen on the target cell followed by toxin that enters and kills the cell.

Thus, an aspect of the present invention relates to an immunotoxin that comprises the antibody of the present invention or a fragment hereof.

Another aspect of the present invention relates to an immunoconjugate comprising the monoclonal antibody of the present invention or a functional fragment thereof.

Antibody conjugates may include use of toxin or other cytotoxic and/or cytostatic groups.

One class of cytotoxic drug immunoconjugates may consist of cytotoxic payloads exemplified by doxorubicin, maytansinoids, calicheamycin, ozogamicin, calicheamicin, geldanamycin, maytansinoids and taxoids as well as peptide exotoxins.

Another class is monoclonal antibodies conjugated to toxin payloads exemplified by pseudomonas exotoxin, abrin, saporin and ricin.

Cells Comprising and Expressing the Antibodies of the Present Invention

The above described DNA molecules or expression vectors can be introduced into host cells.

Such cells can through hybridoma technology become immortalized cells that produce the chimeric or humanized antibodies.

Hybridoma technology is a technology of forming hybrid cell lines (called hybridomas) by fusing a specific antibody-producing B cell with a myeloma (B cell cancer) cell that is selected for its ability to grow in tissue culture and for an absence of antibody chain synthesis.

The antibodies produced by the hybridoma are all of a single specificity and are therefore monoclonal antibodies (in contrast to polyclonal antibodies).

Thus, one aspect of the present invention relates to a host cell carrying one or more vectors or DNA molecules of the present invention.

One embodiment of the present invention relates to a host cell carrying an expression vector comprising a DNA molecule encoding the variable heavy chain of OI-3, and a second expression vector comprising a DNA molecule encoding the variable light chain of the present invention.

In one embodiment of the present invention is the host cell a mammalian cell.

In another embodiment of the present invention is the cell a hybridoma cell.

Pharmaceutical Compositions

Antibodies are usually applied in the treatment of diseases formulated in pharmaceutical compositions.

Such compositions are optimized for parameters such as physiological tolerance and shelf-life.

Thus, relates and aspect of the present invention to a pharmaceutical composition comprising, as the active ingredient, one or more anti-CD146 antibody molecules of the present invention (e.g. the chimeric or humanized antibody derived from OI-3 or a fragment hereof), and a pharmaceutically acceptable carrier.

An embodiment of the present invention relates to a pharmaceutical composition as described above, further comprising one or more additional therapeutic agents.

In another embodiment of the present invention are said one or more additional therapeutic agents selected from agents that induce apoptosis.

A radioimmunotherapeutic product based on murine, chimeric or humanized OI-3 would typically be provided as a pharmaceutical composition consisting of a radionuclide, according to the description above, linked via a chelator to the murine, chimeric or humanized antibody OI-3 dissolved in a buffer solution, which to a substantial degree maintain the chemical integrity of the radioimmunoconjugate and is being physiologically acceptable for infusion into patients.

Thus, an aspect of the present invention relates to a pharmaceutical composition comprising a radioimmunoconjugate of the present invention, and a pharmaceutically acceptable carrier, diluent and/or excipient.

Acceptable pharmaceutical carriers include but are not limited to non-toxic buffers, fillers, isotonic solutions, etc. More specifically, the pharmaceutical carrier can be but are not limited to normal saline (0.9%), half-normal saline, Ringer's lactate, 5% Dextrose, 3.3% Dextrose/0.3% Saline. The physiologically acceptable carrier can contain a radiolytic stabilizer, e.g., ascorbic acid, human serum albumin which protect the integrity of the radiopharmaceutical during storage and shipment.

A further embodiment of the present invention relates to a pharmaceutical composition of the present invention for treating cancer types expressing CD146.

In an embodiment of the present invention the pharmaceutical composition is for treatment of a cancer type selected from the group consisting of osteosarcoma, soft tissue sarcomas, breast cancer, lung cancer, head and neck cancer, melanoma, pancreas cancer, leukemia and brain cancer.

An aspect of the present invention relates to the pharmaceutical composition of the present invention for use in depleting cells that express CD146 on their surface.

Another aspect of the present invention relates to the pharmaceutical composition of the present invention for use in the treatment of autoimmune or inflammatory diseases.

CSPG4 is a clinically evaluated target (Raja et al., 2007), co-expressed in several of the same malignancies as CD146. On all the cell lines tested positive for binding, OI-3 bound as least as good as or better than 9.2.27 on all of them according to the flow cytometry data. Thus, it is indicated that CD146 could be a relevant target for therapy against cancer or other malignancies.

Method of Production

The chimeric or humanized antibodies of the present invention can be produced by several methods.

One method for producing such antibodies comprises transfecting a mammalian host cell with one or more vectors of the present invention, culturing the host cell and recovering and purifying the antibody molecule.

Another method for producing such antibodies comprising construction of hybridoma cells that produce the chimeric or humanized antibodies of the present invention.

Method of Treatment and Uses

Therapeutic use of a pharmaceutical solution according to the present invention may be for treatment against malignant cells expressing CD146, including but not limited to a cancers types selected from the group consisting of osteosarcoma, soft tissue sarcomas, breast cancer, lung cancer, head and neck cancer, melanoma, pancreas cancer, prostate cancer, leukemia and brain cancer.

Other uses could be treatment of autoimmune diseases and treatment of transplantation related effects.

The therapy could be based on immunotherapy, antibody drug conjugate, immunotoxin or radioimmunotherapy including but are not limited to, beta-particle-radiation or alpha-particle-radiation or a combination of these.

The therapy could be administered either as a monotherapy or in combination with other therapies, preferentially standard treatments. Such other therapies may be pretreatment, surgery, chemotherapy (including doxorubicin, vinblastin and gemcitabine), immunotherapy, photodynamic therapy, proteasome inhibitor (including bortezomib), histone deacetylase inhibitors (including vorinostat and suberoylanilide hydroxamic acid), vitamin D3 and vitamin D3 analogs, cell cycle checkpoint inhibitors (including UCN-01 and 2-(4-(4-Chlorophenoxy)phenyl)-1H-benzimidazole-5-carboxamide), hypoxic cell radiosensitizers (including metronidazole and misonidazole), apoptosis inducers (including withaferin A) radiosensitizers, radioimmunotherapy or a combination of two or more of these.

By administered is meant intravenous infusion or intravenous injection. More specifically, the OI-3 based therapeutic of the present invention can be administered directly in a vein by a peripheral cannula connected to a drip chamber that prevents air embolism and allows an estimate of flow rate into the patient.

In one embodiment the OI-3 based therapeutic can be administered in a repeated fashion.

In another embodiment of the present invention the OI-3 based therapeutic could be administered in a repeated fashion but with different modalities, e.g., beta-radioimmunotherapy could be followed by alpha-radioimmunotherapy or vice versa or cytotoxic drug conjugate followed by immunoconjugate etc.

An aspect of the present invention relates to the use of the OI-3 based therapeutic of the present invention for the treatment of cancer.

Another aspect of the present invention relates to the use of the OI-3 based therapeutic of the present invention as a medicament.

An embodiment of the present invention relates to the use of the OI-3 based therapeutic of the present invention administered in combination with or in addition to other therapy.

In an embodiment of the present invention the other therapies is selected from pretreatment, chemotherapy, monoclonal antibody therapy, surgery, radiotherapy, and/or photodynamic therapy.

In another embodiment of the present invention the other therapies are bone marrow transplantation or stem cell transplantation and/or therapy.

In an embodiment of the present invention is the pretreatment done by administering the chimeric or humanized antibody of the present invention followed by treatment by OI-3 based therapeutic.

An aspect of the present invention relates to a method for treatment of a cancer type selected from the group consisting of osteosarcoma, soft tissue sarcomas, breast cancer, lung cancer, head and neck cancer, melanoma, ovarian cancer, colorectal cancer, mesothelioma, glioblastoma, pancreas cancer, leukemia and brain cancer, comprising administration of an effective amount of the pharmaceutical composition of the present invention.

In one embodiment of the present invention are the uses and methods of treatment of the present invention performed in vitro or ex vivo.

In an embodiment of the present invention the antibody dosing is 1-1000 mg per patient, more preferably 5-50 mg per patient, and radionuclide, for example $^{177}$Lu, amounting to 1-200 MBq/kg, more preferably 10-100 MBq/kg of bodyweight.

The pharmaceutical compositions of the present invention comprising the chimeric or humanized antibody of the present invention can be used in depleting cells that express CD146.

Such pharmaceutical compositions can be used in the treatment of cancer.

The cancer types may be selected from the group consisting of osteosarcoma, soft tissue sarcomas, breast cancer, lung cancer, head and neck cancer, melanoma, pancreas cancer, leukemia and brain cancer.

An embodiment of the present invention relates to a pharmaceutical composition comprising the murine, chimeric or humanized antibody of the present invention for use in the treatment of autoimmune or inflammatory diseases that involve cell expression CD146 in their pathology.

Another embodiment of the present invention relates to a method of depleting CD146 expressing cells from a population of cells, comprising administering to said population of cells an antibody molecule of the present invention a pharmaceutical composition containing such antibody molecule.

Yet another embodiment of the present invention relates to a method for treating a patient suffering from a cancer type selected from the group consisting of osteosarcoma, soft tissue sarcomas, breast cancer, prostate cancer, lung cancer, head and neck cancer, melanoma, pancreas cancer, leukemia, ovarian cancer, colorectal cancer, mesothelioma, glioblastoma and brain cancer, comprising administering to said patient an effective amount of a pharmaceutical composition comprising the murine, chimeric or humanized antibody of the present invention.

Another embodiment of the present invention relates to the treatment of metastatic cancer in bodily cavitites e.g., peritoneal cavity, thorax/pleural cavity and cranial cavity.

A further embodiment of the present invention relates to intracavitary administration of antibody, conjugates or compositions of the present invention.

Examples of such administrations are intraperitoneal, intrapleural, and intracranial administrations.

In a special embodiment a murine, chimeric or humanized OI-3 is administered to a patient, prior to therapy with a radiolabeled or an immuntoxin version of murine, chimeric or humanized OI-3, to block normal tissue cells and improve tumor uptake.

The dosing should be sufficient to block normal tissue uptake but not excessive as this would reduce the tumor uptake. E.g. the murine, chimeric or humanized OI-3 should be given in a dosage between 0.5 mg and 1 g per patient.

It could be given e.g. one week before and/or 1-5 hours before the administration of the cytotoxic or cytostatic immunoconjugate.

The OI-3 and derivatives thereof may be used for detection and/or treatment of cancer with elevated expression of CD146, including but not limited to osteosarcoma, soft tissue sarcomas, breast cancer, lung cancer, head and neck cancer, melanoma, pancreas cancer and brain cancer.

This includes treatment of primary cancer, metastatic cancer and cancer stem cells. In some instances it may also be used for treatment of non-cancerous diseases. The treatment may be given systemically or as a local or intralesional application and also includes limb perfusion treatment.

In one embodiment the OI-3 antibody or derivates thereof is used for immunopurging of cancer cells form the blood or bone marrow or ascites from cancer patients. Immunopurging may include use of antibody conjugated to magnetic micro- or nanoparticles allowing magnetic separation during the purging procedure. Immunopurging may e.g. be used for therapeutic purification bone marrow, blood or autologous stem cells before returning to patients undergoing stem cell transplantation. Immunopurging may also be used for detecting antigen or cancer cells in blood, bone marrow, ascited or other body fluids.

A further aspect of the present invention relates to a method of inhibiting the growth of a cancer cell, comprising; contacting the cancer cell with an effective amount of an antibody of the present invention, thereby inhibiting the growth of the cancer cell.

Another aspect of the present invention relates to a method of depleting CD146 expressing cells from a population of cells, comprising administering to said population of cells an antibody molecule of the present invention or a pharmaceutical composition containing such antibody molecule.

In one embodiment of the present invention are the methods carried out in vitro.

The administration of the antibodies and pharmaceutical compositions of the present invention can be done through many different routes of administration including topical, oral, through the gastrointestinal tract, intradermal, subcutaneous, nasal, intravenous, intramuscular, enteral or parenteral.

A special aspect of the present invention is a method of treating cancer with radiolabeled OI-3 or derivatives thereof to cause upregulation of antigens in cancer cells from solid tumors, including HER-2 and EGFR and a combination therapy of radiolabeled OI-3 and derivatives thereof and HER-2 or EGFR targeting antibody as a co-treatment or follow-up treatment.

Method of Diagnosis, Indication, IHC and Imaging

The present invention also includes immunoconjugates e.g., radioactive conjugates for therapy. In a special embodiment it may be a radioactive conjugate for imaging useful for PET or SPECT. In another embodiment it may be a non-radioactive conjugate useful for imaging, e.g., by MR.

The OI-3 antibody or derivatives may be used for in vitro applications, e. g., diagnostic use, and in vivo applications. In vivo applications may include immunotherapy, antibody conjugate therapy and in vivo imaging.

Thus one aspect of the present invention relates to a method of diagnosing of cancer in a subject, comprising contacting a sample from the subject with the isolated monoclonal antibody the present invention or functional fragment thereof, and detecting binding of the isolated monoclonal antibody or functional fragment thereof to the sample, wherein a significant increase in binding of the isolated monoclonal antibody or functional fragment thereof to the sample as compared to binding of the isolated human monoclonal antibody or functional fragment thereof to a control sample diagnoses the subject with cancer.

Another aspect of the present invention relates to a method of detecting cancer or confirming the diagnosis of cancer in a subject, comprising contacting a sample from the subject with the isolated monoclonal antibody of the present invention or functional fragment thereof, and detecting binding of the isolated monoclonal antibody or functional fragment thereof to the sample, wherein a significant increase in binding of the isolated monoclonal antibody or functional fragment thereof to the sample as compared to binding of the isolated human monoclonal antibody or functional fragment thereof to a control sample detects cancer in the subject or confirms the diagnosis of cancer in the subject.

A further aspect of the present invention relates to a method of indicating cancer in a subject, comprising; contacting a sample from the subject with the isolated monoclonal antibody of the present invention or functional fragment thereof, and detecting binding of the isolated monoclonal antibody or functional fragment thereof to the sample, wherein a significant increase in binding of the isolated monoclonal antibody or functional fragment thereof to the sample as compared to binding of the isolated human monoclonal antibody or functional fragment thereof to a control sample indicates cancer in the subject.

It should be noted that an indication does not necessarily involve an evaluation of a medical professional.

In one embodiment of the present invention is the isolated monoclonal antibody or functional fragments thereof directly labelled.

Another embodiment of the present invention relates to a method as described above further comprising, contacting a second antibody that specifically binds the isolated monoclonal antibody or functional fragment thereof, with the sample, and Detecting the binding of the second antibody, where a significant increase in binding of the second antibody to the sample as compared to binding of the second antibody to a control sample indicates or detects cancer in the subject or diagnosis the subject with cancer.

In one embodiment of the present invention is the cancer type selected from the group including but not limited to a cancers types selected from the group consisting of osteosarcoma, soft tissue sarcomas, breast cancer, Prostate cancer, lung cancer, head and neck cancer, melanoma, pancreas cancer, leukemia and brain cancer.

In another embodiment of the present invention is the sample a biopsy, stool, blood, serum, or urine.

The types of diagnosis and imaging includes flow cytometry, IHC, MR scanning and all other types of imaging that where antibodies can be detected in a sample.

Kits

An aspect of the present invention relates to a kit for the production of the radioimmunoconjugate of the present invention comprising two or more vials, wherein one vial contains a conjugate comprising a chelator linked to a murine monoclonal antibody OI-3; and a second vial comprising a radionuclide.

One embodiment of the present invention relates to the kit as described above, wherein the radioimmunoconjugate is generated by mixing the content of the two vials.

Another aspect of the present invention relates to an injectable preparation of chimeric or humanized OI-3 useful for pretreatment, to block CD146 in normal tissues before radioimmunotherapy with radiolabeled or immunotoxic versions of OI-3, comprising at least 0.5 mg and not more than 1 g of antibody.

A kit may require some procedures to be performed, e.g., radiolabeling and/or purification to take place before infusion.

An embodiment of the present invention relates to a kit of the present invention, wherein the content of one or several of the vials are either lyophilized or in a solution.

By mixing the contents of the two vials to generate the radioimmunoconjugate the final product will appear. Thus, in another embodiment of the present invention the radioimmunoconjugate is generated by mixing the content of the two vials.

This product may need purification prior to use.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1

Immunization, Fusion and Selection of Antibody Producing Hybridoma Clone

Animals were immunized initially with human osteosarcoma cells and later with extracts of cellular membrane proteins. Spleen cells from the immunized mice were fused with myeloma cells according to standard procedure for generation of hybridoma cells.

Supernatants of all growing hybridoma clones of the fusions were tested by flow-cytometry for binding to cancer cell lines. (General protocol for cultivation of cells and flow cytometry see Example 4).

Supernatants of positive clones were further selected by verifying that the antibodies showed no binding to isolations of human peripheral blood mononuclear cells (PBMC).

Selected clones were propagated through repeated expansion and recloning and purification and tested on a broader panel of cancer cell lines by flow cytometry as well as PBMC from additional individuals (described in Example 4).

One of the clones, OI-3, was found to bind to osteosarcoma and melanoma cells and were subcloned and retested until a clone yielding relevant immune reactivity was identified. This was expanded and stocks were collected and frozen in liquid nitrogen.

Example 2

Sequence Identity of the Variable Chains of the OI-3 Murine Monoclonal Antibody

The coding DNA sequences of the variable heavy (VH) and light (VL) chain of the OI-3 mAb produced by hybridoma clone 3_45 (original annotation) was determined by sequencing of RNA from hybridoma subclone 3_45 (A7) and subclone 3_45 (C2). The VH and VL sequences achieved from 3_45 (C2) and 3_45 (A7) are identical, confirming the identity of OI-3.

Total RNA was extracted from frozen hybridoma cells and reverse transcribed into cDNA using universal primers. RACE was then performed on the cDNA to amplify the variable antibody fragments. Ten clones for each variable fragment were sequenced to confirm the identity.

The nucleic acid sequences encoding the variable heavy chain and the light heavy chain are SEQ ID NO: 1 and SEQ ID NO: 2, respectively.

The amino acid sequences corresponding to the variable heavy chain and the light heavy chain are SEQ ID NO: 3 and SEQ ID NO: 4, respectively.

The variable heavy chain (SEQ ID NOs 1 and 3).

```
atgggatggatctggttctttctcttcctcctgtcaggaactgca
 M  G  W  I  W  F  F  L  F  L  L  S  G  T  A ggtgtccactctgaggtccagttgcagcagtctggacctgagcta
 G  V  H  S  E  V  Q  L  Q  Q  S  G  P  E  L gtgaagactggggcttcagtgaagatatcctgcaaggcttctggt
 V  K  T  G  A  S  V  K  I  S  C  K  A  S  G tactcattcactggttactacatacactgggtcaagcagagccat
 Y  S  F  T  G  Y  Y  I  H  W  V  K  Q  S  H ggaaagagccttgagtggattggatatattagtaattacaatggt
 G  K  S  L  E  W  I  G  Y  I  S  N  Y  N  G gctactacctacagccaggagttcaagggcaaggccacatttact
 A  T  T  Y  S  Q  E  F  K  G  K  A  T  F  T gtagacagatcctccaggatagcctacatgcagttcaccggcctg
 V  D  R  S  S  R  I  A  Y  M  Q  F  T  G  L acatctgaagactctgcggtctattactgtgcgggtaacagctgg
 T  S  E  D  S  A  V  Y  Y  C  A  G  N  S  W ggtgactggtacttcgatgtctggggcgcagggaccacggtcacc
 G  D  W  Y  F  D  V  W  G  A  G  T  T  V  T gtctcctca
 V  S  S
```

The variable light chain (SEQ ID NOs 2 and 4).

```
atgaagttgcctgttaggctgttggtgctgatgttctggattcct
 M  K  L  P  V  R  L  L  V  L  M  F  W  I  P
```

-continued

```
gcttccagcagtgatgttgtgatgacccaaactccactctccctg
 A  S  S  S  D  V  V  M  T  Q  T  P  L  S  L cctgtcagtcttggagatcaagcctccatctcttgcagatctagt
 P  V  S  L  G  D  Q  A  S  I  S  C  R  S  S cagagccttgtacacagtaatggaaacacctatttacattggtac
 Q  S  L  V  H  S  N  G  N  T  Y  L  H  W  Y ctgcagaagccaggccagtctccaaagctcctgatctacaaagtt
 L  Q  K  P  G  Q  S  P  K  L  L  I  Y  K  V tccaaccgatttctggggtcccagacaggttcagtggcagtgga
 S  N  R  F  S  G  V  P  D  R  F  S  G  S  G tcagggacagatttcacactcaagatcagcagagtggaggctgag
 S  G  T  D  F  T  L  K  I  S  R  V  E  A  E gatctgggagtttatttctgctctcaaagtacacatgtttccacg
 D  L  G  V  Y  F  C  S  Q  S  T  H  V  S  T ttcggagggggaccaagctggaaataaaa
 F  G  G  G  T  K  L  E  I  K
```

Example 3

Determination of IgG Subclass for the OI-3 Antibody

Flow cytometry analyses with fluorochrome conjugated murine isotype specific secondary antibodies (IgG1, IgG2a, IgG2b, IgG3, and IgM) were performed. OI-3 was determined to be isotype IgG1. FIG. 1. (General protocol for cultivation of cells and flow cytometry see Example 4).

Example 4

Expression Analysis of OI-3 in a Panel of Human Tumor Cell Lines and Fresh PBMC Preparations Three human melanoma cell lines (A375, MelJRpost3.3 and WM239), three osteosarcoma (OHS, KPDX and SAOS-2), three breast cancer (BT-474, MCF-7 and MDA-MB-231), four lymphoma cell lines (Daudi, Raji, Rec-1 og DOHH2), one ovarian cancer cell line (SKOV-3), one pancreatic cell line (PANC-1) and one squamous cancer cell line (SCC-4) were tested for OI-3 expression. Cells were obtained from either the American Type Culture Collection (ATCC, Manassas, Va., USA) or the Department of Tumor Biology at the Norwegian Radium Hospital, Oslo, Norway (MelJRpost3.3 Lai et al., 2012, WM239 Herlin et al., 1990, OHS Fodstad et al., 1986, KPDX Bruland et al., 1985).

Cells were grown in DMEM or RPMI Gibco (Invitrogen), supplemented with 10% FCS, and with extra glutamine (Glutamax) and antibiotics (Pen/Strep) dependent on the recommendation of the supplier. Cells were grown in a humid atmosphere with 95% air and 5% CO2. Adherent cell lines were harvested at 80-100% confluence by 2× wash in DPBS followed by trypsination (TrypLE express, Invitrogen). Cells grown in suspension were harvested by centrifugation.

Peripheral blood mononuclear cells (PBMC) from three individuals were analysed. Whole blood drawn on EDTA glass from healthy donors was diluted 1:1 with DPBS (DPBS, Hyclone, Thermo Scientific, USA) in a 50 ml tube. Diluted whole blood was layered on top of Lymphoprep (Medinor, Norway) in a ratio 2:1 in a 50 ml tube and centrifuged at 1000×g for 20 min with slow braking. The mononuclear cells from the interface are aspirated and washed twice with DPBS (300×g, 10 min). The pelleted cells are gently resuspended in culture medium (RPMI-1640 with 10% heat-inactivated fetal bovine serum) using a pipette. Cell numbers were determined by counting of aliquots on Countess (Invitrogen) followed by dilution in flow buffer (Dulbecco's PBS w/0.5% BSA, 0.1% NaN3). 200.000 cells pr sample well was distributed in a 96 well plate (Becton Dickinson PRO-BIND 96).

Secondary antibody (anti-mouse IgG (whole molecule) F(ab')2 fragment-FITC) was added and incubated for 30 min and washed as in previous step. Washed cell pellets were dissolved in 150 ul flow buffer and analysed on FACS Calibur. All wash steps were performed by centrifugation at 1.200 rpm in 5 min.

OI-3 binds to all melanoma and osteosarcoma cell lines tested, as well as to a triple-negative breast cancer cell (MDA-MB-231), a pancreatic (PANC-1) and a squamous cancer cell line (SCC-4) Table 1. The OI-3 antibody does not bind to the two other breast cancer cell lines (MCF-7 and BT-474), to the ovarian cancer cell line (SKOV-3) nor the lymphoma cell lines (Daudi, Raji, Rec-1 and DOHH2). OI-3 showed no binding to PBMC from three different individuals (FIG. 2).

TABLE 1

Measured binding of OI-3 antibody to a panel of human tumor cell lines by flow cytometric analysis

| Tissue type | Cell line | Cancer type | OI-3 binding |
|---|---|---|---|
| Skin | A375 | malignant melanoma | yes |
|  | WM239 | metastatic melanoma | yes |
|  | MelJRpost 3.3 | malignant melanoma | yes |
| Bone | OHS | osteosarcoma | yes |
|  | KPDX | osteosarcoma | yes |
|  | Saos-2 | osteosarcoma | yes |
| Ovary | SKOV-3 | adenocarcinoma | no |
| Mammary gland | MDA-MB-231 | adenocarcinoma, metastatic site | yes |
|  | MCF7 | adenocarcinoma, metastatic site | no |
|  | BT-474 | ductal carcinoma | no |
| Lymfoblast | Daudi | Burkitt's lymphoma | no |
|  | Raji | Burkitt's lymphoma | no |
|  | Rec-1 | mantle cell lymphoma | no |
|  | DOHH2 | follicular lymphoma, B cell | no |
| Pancreas | PANC-1 | epitheloid carcinoma | yes |
| Tongue | SCC-4 | squamous cell carcinoma | yes |
| Peripheral blood | PBMC (3 ind.) | normal | no |

Example 5

Identification of OI-3 Target Antigen by Western Blotting

Protein lysates were made from one human osteosarcoma (OHS) and one human melanoma (A375) cell line and one ovarian cancer cell line (SKOV-3). About 10 million cells were harvested and lysed with 150 µl Pierce IP lysis buffer (Thermo Scientific, Rockford, Ill. USA) with 1× Halt proteinase inhibitor (Thermo Scientific) at 4° C. for 30 minutes before centrifugation at 13.000×g for 5 minutes followed by collection of the supernatant from the pelleted debris. Protein samples were diluted in NUPAGE Sample Buffer×4 (BioRad, Hercules, Calif., USA), boiled for 5 minutes, separated by SDS-PAGE Criterion XT, 4-12% (BioRad) and transferred to PVDF membrane by semi-dry transfer. The membrane was then blocked with 5% dry milk in PBS-T (blocking buffer) to prevent unspecific binding, followed by incubation with antibody OI-3 at a concentration of 2.5 µg/ml overnight at 4° C. The membrane was washed 4 times in blocking buffer and then incubated with peroxidase conjugated anti-mouse secondary antibody (Jackson ImmunoResearch Laboratories, West Grove, Pa., USA) in blocking buffer. Detection of secondary antibody was done using SuperSignal West Pico substrate (Thermo Scientific) and visualization was done using Molecular Imager® ChemiDox™ XRS+(Bio Rad). A protein band of approximate 110 kDa was detected by OI-3 binding in the lysates of the osteosarcoma (OHS, lane 1 FIG. 3A) and melanoma (MelJRpost3.3, lane 2 FIG. 3A) cell lines. No band was visible in the lysate from the ovarian cancer cell line SKOV-3 (lane 3). Lane 4 is empty (no sample). Lane 5 with MagicMark XP Western Protein Standard (Invitrogen). Sizes of bands of the protein standard are shown on the right hand side. Based on the expression pattern in human tumor cell lines described in Example 4, and the specific binding to a protein of 110 KDa by Western blotting analysis, a commercial lysate of cells overexpressing the antigen CD146/MCAM/MUC-18 was purchased (OriGene, Rockville, Md.), and also murine monoclonal anti-CD146 antibody (P1H12, eBioscience, San Diego, Calif., USA) and a rabbit monoclonal antibody against CD146 (EPR3208, Origene). Identical protein bands, at about 110 kDa, were detected by OI-3 (lane 1-4), P1H12 (lane 5-8) and EPR3208 (lane 9-12) antibodies in lysates from CD146 overexpressing cells (lane 1, 5, 9), lysates of melanoma (MelJRpost3.3, lane 3, 6, 11) and osteosarcoma cells (OHS 4, 8, 12) (FIG. 3B). No bands were observed for in any of the blots for the samples with control lysates (vector transfected lysate control, Origene, lane 2, 6 and 11, FIG. 3B). These results further support the target antigen of OI-3 to be CD146.

Immunoprecipitation was performed with Dynabeads protein G (Invitrogen), basically as described by Wang et al., 1999. A MelJRpost3.3 lysate was prepared as described for the Western analysis. Initially, a preclearance was performed with Dynabeads protein G and lysate of $30 \times 10^6$ cells dissolved in 1 ml DPBS w/0.5% BSA for to remove proteins of the lysate that bind non-specific to the beads. After 15 min incubation at 4° C. the lysate was removed from the beads by magnetic separation. 4 µg OI-3 was added to the lysate and incubated for 3 h with slow rotation on a Hulamixer at 4° C. Non-bound lysate was removed by magnetic separation, and the beads was washed 1× w/ 0.75 ml lysis buffer (the solution was transferred to a clean eppendorf tube) followed by 1× wash with 0.5 ml DPBS. Control samples of protein bound non-specific to Dynabeads G, Dynabeads G with OI-3, but no lysate etc were all prepared for SDS-page by addition of Lamenni sample buffer and β-mercaptoethanol and denatured at 95° C. for 5 min before application on a 4-15%, 18 well Criterion TGX gel. After run the gel was stained with Coomassie blue. One strong band of approximately 110 kDa was observed in addition to bands of 25 and 50 kDa (light and heavy chain of OI-3). This assay further support that CD146 is the target of OI-3.

Example 6

Immunohistochemical Studies (IHC)

Procedures for IHC staining of Frozen Tissue sections: Tissues from a metastatic mouse model (SCID) of human MelJRpost3.3 was snap frozen (OCT-isopentane before transfer to liquid nitrogen and storage in −80° C. freezer until use). 5 µM sections of frozen tissue were air dried for one hour before being fixed in acetone at room temperature for 10 minutes. Slides were then dried at room temperature for 10 min. After 2×5 min. washes in 0.5 M Tris, the endogenous peroxidase activity was blocked using 3% $H_2O_2$ in methanol for 10 min. Sections were washed with distilled water and then 1×5 min with 0.5 M Tris. Sections were blocked with 5% BSA in PBS for 20 min. The slides were then incubated with horseradish peroxidase (HRP) conjugated OI-3 (10 µg/ml) in 2.5% BSA in for 60 min at room temperature. Sections were washed 2×5 min with 0.5M Tris, and then incubated with liquid DAB and Chromogen system (Dako K3468) for 5 min; 1 drop of DAB+Chromogen in 1 ml of substrate buffer (supplied by Dako). Sections were rinsed in distilled water, counterstained with hematoxylin for 1-2 min, following removal of the excess staining with 0.1% HCl in EtOH and rinsing in cold tap water for 10 min. Sections were dehydrated in EtOH, then in xylene and mounted in Perfix. Procedures for IHC staining of Paraffin embedded tissue sections: Tissues were fixed in 10% neutral buffered formalin for 24 h, then routinely processed, embedded in paraffin blocks and cut into 4 µM thick sections. Tissue sections were deparaffinised with Tissue clear and EtOH and washed in distilled water. Sections were incubated with 3% $H_2O_2$ in methanol for 10 min to block endogenous peroxidase activity, followed by rinsing in distilled water. Slides were then treated with 0.01 M Citric acid at pH 6.0 for antigen retrieval; slides were placed in the microwave oven set at high heat, 2×5 min, and then cooled down for 20 min. Slides were rinsed for 1 min in tap water followed by a rinse in 0.5 M Tris for 5 min. Slides were blocked with 5% BSA in PBS for 20 min, before antibody staining as described above.

Lung tissue with visible tumors from the MelJRpost3.3 metastatic model was analysed as well as a paraffin sections from a patient with superficial spreading of malignant melanoma (Clark IV). Results are presented in FIG. 4. Positive staining with membrane localization was observed for OI-3 to both paraffin-embedded and frozen sections of metastasis of the lung of the SCID mice. The staining of paraffin sections from the patient sample showed more diffuse but positive staining.

This shows that OI-3 has suitable properties for the detection of cancer cells in immunohistochemistry analyses.

Example 7

Radiolabeling of OI-3

A. Radiolabeling of OI-3 with $^{125}I$

An iodogen tube (Pierce) was washed with 1 ml tris-buffer and subsequent added 100 µl tris buffer (pH 7.5) and added $^{125}I$ iodine. The solution was swirled gently in the tube a few times during a 6 minutes period where after some or all of the $^{125}I$ solution was added to a vial with typically 100 µl tris with 50-200 µg OI-3 antibody.

Using occasional swirling of the vial, the reaction went on for 7 minutes. After that 50 µl I-tyrosine (saturated) in tris was added and reacted for at least 5 minutes before the solution was purified using a Spehadex G-25 PD-10 (GE Health) size exclusion column.

About 70% of the activity would elute in the high molecular weight fractions and was collected and tested for immunoreactivity and used in cell binding experiments.

B. Radiolabeling of Bn-DOTA Conjugated OI-3 p-SCN-Bn-DOTA (Macrocyclics) was conjugated to OI-3 according to published procedures. Briefly, OI-3 antibody in NaCl was added carbonate buffer to adjust the pH to approximately 8.5 and an antibody concentration of 3-5 mg/ml. A 4 times molar excess of p-SCN-Bn-DOTA was added and the reaction vial was mixed gently on a thermomixer (Eppendorf) for 1-2 hours at room temperature.

The reaction was terminated with 0.2 M glycine in carbonate (pH 8.5) and purified by several cycles of ultrafiltration using a centrifugal filter device (Vivaspin 20, 50 kDa MWCO, Sartorius Stedim). During the filtration the solvent was changed to isotonic NaCl for the chelator-antibody conjugate. Thereafter the pH was adjusted to 5.5-6.0 by adding ammonium acetate and cationic $^{177}$Lu in diluted HCl was added and reacted for 15 minutes at 37° C. This would yield a product of 90-100% radiochemical yield (If less than 95% gel filtration purification with Sephadex PD-10 was performed).

In conclusion: The OI-3 monoclonal antibody could be radiolabeled via both thyrosine and lysine with a good retention of binding properties. This indicates that it may be appropriate for creating immunoconjugates for therapy etc.

Example 8

Cell Binding with Radiolabeled OI-3

The human cancer cells lines MelJRpost 3.3 (melanoma) OHS (osteosarcoma) and MDA-MB-231 (breast adenocarcinoma) were used to study binding of radiolabeled OI-3 monoclonal antibody.

The cell lines were grown as monolayers in plastic flasks supplied with RPMI 1640 medium/fetal calf serum etc and kept in 5% CO2 incubators. After trypzinisation, cells were centrifuged, the supernatant removed and the cells resuspended in Dulbecco's PBS with 0.5% bovine serum albumin (DPBS/BSA).

Cell concentrations were adjusted to 25-50 million cells per ml. Two-hundred and fifty microliter cell suspension was added to 4 ml reactions tubes. To duplicates were added 2 micrograms of (1) HH1 irrelevant IgG1 (Smeland et al., 1985). Each tube was whirl-mixed for 5 seconds and then put on a shaker for approximately 20 minutes to pre-saturate the antigen.

Thereafter approximately 2.7 nanogram of $^{125}$I-labeled OI-3 was added to each tube. Thereafter each tube was whirlmixed for 5 seconds, and incubated at a shaker for 1-2 hours. After that each tube was counted on a gamma counter to determine applied activity, washed tree times with 0.5 ml DPBS/BSA and recounted for determining cell bound fraction.

Results: The cell bound fraction varied between 40 and 80% (Table 2).

In conclusion radiolabeled OI-3 displayed a relevant binding (immunoreactive fraction) in cell binding assays.

TABLE 2

Binding of $^{125}$I-OI-3 to Triple negative breast cancer cell line (MDA-MB-231), melanoma cell line (MelJRpost3.3) and osteosarcoma (OHS) after pre-treatment of the cell lines with cold antibodies.

| Pretreatment | MDA-MB-231 | MelJRpost3.3 | OHS |
| --- | --- | --- | --- |
| HH1 irrelevant IgG | 100% | 100% | 100% |
| OI-3 | 12% | 11% | 12% |

Data for $^{125}$I-OI-3 and HH1 irrelevant IgG was normalized to 100%.

Example 9

Antigen/Epitope Blocking Assay

The human cancer cells lines MelJRpost3.3 (melanoma) and OHS (osteosarcoma) were used to study blocking of OI-3 binding to target antigen. The cell lines were grown as monolayers in plastic flasks supplied with RPMI 1640 medium/fetal calf serum etc and kept in 5% CO2 incubators. After trypzination, cells were centrifuged, the supernatant removed and the cells re-suspended in Dulbecco's PBS with 0.5% bovine serum albumin (DPBS/BSA). Cell concentrations were adjusted to approximately 10 million cells per ml. Two-hundred microliter cell suspension was added to 4 ml reactions tubes. Initially, a blocking assay were performed with a mix of commercially available anti-CD146 antibodies (mouse monoclonal anti-CD146 (P1H12), mouse monoclonal anti-Mel-CAM (OJ97cMUC18), rabbit monoclonal anti-CD146 (ERP3208), rabbit polyclonal anti-Mel-Cam (H-62). The assay was run in duplicate, adding 10 µg of each blocking antibody. Negative control samples were run with a mix of antibodies known to bind antigens on OHS cells (murine monoclonal anti-CSPG4 (LHM-2 and 9.2.27, Erbitux). 10 µg of each antibody was added to the control samples. The LHM-2 and 9.2.27 antibodies binds to MelJRpost3.3, Erbitux does not, but was included in the blocking experiment of OI-3 binding to this cell line. Each tube was whirl-mixed for 5 seconds and then put on a shaker for approximately 20 minutes to pre-saturate the antigen. Thereafter approximately 2.7 nanogram of $^{125}$I-labeled OI-3 was added to each tube. Thereafter each tube was whirl-mixed for 5 seconds, and incubated at a shaker for 30-60 minutes. After that each tube was counted on a gamma counter to determine applied activity, washed tree times with 0.5 ml DPBS/BSA and recounted for determining cell bound fraction.

The first data presented in Table 3 show that binding of $^{125}$I-OI-3 is was significantly blocked by the mix of antibodies against CD146, both on MelJRpost3.3 and OHS cells, whereas the mix of antibody against CSPG4 and EGFR did not show significant blocking of $^{125}$I-OI-3 (the level of background of $^{125}$I-OI-3 binding to cells pretreated with cold OI-3 was less than 2% in the assay). The experiment was repeated with preincubation of MelJRpost3.3 with mouse monoclonal anti-Mel-CAM (OJ97cMUC18) and rabbit polyclonal anti-Mel-Cam (H-62) in separate samples. The murine monoclonal anti CD-146 tested did not block binding of OI-3, whereas the polyclonal antibody, when used for pretreatment alone, reduced the binding to 57%. The specific reduction in OI-3 binding for samples treated with anti-CD146 antibodies, further support that $^{125}$OI-3 targets the CD146 antigen. It should be noted that the CD146 antibodies only reduced binding and not caused a complete blocking which is consistent with the hypothesis that OI-3 targets a unique epitope and that other CD146 antibodies only cause steric hindrance of the binding when the cells are pre-treated with saturable amounts of mixtures of CD146 antibodies.

TABLE 3

Specific binding in % of $^{125}$I-OI-3 after pre-treatment with antibodies.

| Pretreatment | MelJRpost3.3 | OHS |
| --- | --- | --- |
| Mix of anti-CD146 antibodies | 30% | 35% |
| Mix of anti-CSPG4 and EFFR antibodies | 99% | 95% |

TABLE 3-continued

Specific binding in % of $^{125}$I-OI-3 after pre-treatment with antibodies.

| Pretreatment | MelJRpost3.3 | OHS |
|---|---|---|
| rabbit polyclonal anti-Mel-CAM (H-62) | 58% | n/a |
| mouse monoclonal anti-Mel-CAM (OJ97cMUC18) | 101% | n/a |
| OI-3 | 3% | 2% |

Data for specific binding of $^{125}$I-OI-3 without any pretreatment was set to 100%

Example 10

Comparative Expression of OI-3 and a Commercial Anti-CD146 Antibody on Selected Target Cell Lines The selective binding of OI-3 has been evaluated by flow cytometric analysis of a panel of tumor cell lines as described in Example 4. Comparative expression analysis by flow cytometric analysis was performed with OI-3 and commercial murine monoclonal anti-CD146 (OJ79c MUC18). The analysis was performed as described in Example 4, with primary antibodies added at a concentration of 10 µg/ml to approximately 200.000 cells, and incubated for 30 min followed by 2×wash in flow buffer. Secondary antibody (anti-mouse IgG (whole molecule) F(ab')2 fragment-FITC) was added and incubated for 30 min and washed as in previous step and dissolved in 150 ul flow buffer and analysed on FACS Calibur. Both OI-3 and OJ79c MUC18 are murine IgG1 antibodies, and anti CD37 (HH1), a B cell specific IgG1 antibody was used in paralleled control samples. Three melanoma, one osteosarcoma and three breast cancer cell lines were analysed. All cell lines showed similar binding pattern (histogram profiles) for OI-3 and OJ79c MUC18, FIG. 5. MCF-7 and BT-474 showed no or low binding of the antibodies. The similarity in binding pattern of the antibodies to the cell lines support the specificity of OI-3 to CD146, even though the experiment of Example 6 shows that the antibodies do not bind to the same epitope.

Example 11

Comparative Expression of OI-3 to Human Cancer Cell Lines Relative to Other Osteosarcoma and Melanoma Specific Antibodies The binding property of OI-3 has been compared by flow cytometric analysis with antibodies that have been previously studied as RadioImmumoConjugates (RIC) candidates for treatment of osteosarcoma (anti-p80; TP-3, Bruland et al., 1988) and melanoma (anti-CSPG4; 9.2.27, sc-8003, Santa Cruz Biotechnology, Inc). A B-cell specific anti-CD37 marker was used as negative/isotype control (HH1). The assays were performed as described in Example 4. As documented in Example 4, OI-3 binds to all melanoma and osteosarcoma cell lines tested, as well as to a triple-negative breast cancer cell shown to be CSPG4 positive (MB-231, Wang et al., 2010), see Table 1. CSPG4 is documented to be expressed also on osteosarcoma cell lines (Godal et al., 1986). Three cell lines that are double positive for OI-3 and 9.2.27 (MelJRpost3.3, MDA-MB-231 and OHS) was analysed, FIG. 6. OI-3 showed higher intensity than 9.2.27 on all three cell lines, and also higher intensity than TP-3 on the OHS cell line. This indicates that the antigen and epitopes targeted by OI-3 could be relevant in cancer detection and therapy and that OI-3 has favourable properties as a targeting agent.

Example 12

Affinity Assessment Using $^{125}$I-OI-3 and Melanoma Cells In Vitro

A cell suspension of 10 million Mel 3.3 cells per ml in DPBS/0.5% BSA was prepared. To 4 ml tubes were added 200 µl of cell suspension. As control cells pre-treated with 24 µg of OI-3 was used. Six concentrations of $^{125}$I-OI-3 were prepared ranging from 2 ng to 6252 ng per tube.

After approximately two hours the cells were counted for total activity, washed three times with 0.5 ml DPBS/0.5% BSA using centrifugation and removal of supernatant and finally recounted for cell bound activity. The net cell bound activity was determined by subtracting the counts of the blocked cell pellet from the unblocked pellets at the same activity levels.

Results:

From the % bound activity was the molar concentration derived by using an adjustment factor of 5000 to standardize to nmol/L (nM) for each tube. The reactive free concentration was adjusted for the immunoreactive fraction of the $^{125}$I-OI-3 batch used of approximately 0.6. The data are presented in FIG. 7.

Using binding data from incubating cells with various amounts of antibody containing radioactive tracer the cell bound activity was measured at approximate equilibrium after two hours of mixing.

At Equilibrium the following approximation was used: Ka=1/Kd also Kd=½ βmax.

Thus a βmax of approximately 3.0 would yield (from interpolation of binding plot) a kd of 3.1 nM which translates into a Ka of about 3.2×10$^8$M−1 (These numbers seems to be in good agreement with the Scatchard plot were the interception point at X-axis is about 3.1 nM=Kd). The Kd is within the same range as marketed therapeutic antibodies; Rituximab Kd=8 nM (Rituxan, Prescribing information; Genentech, Inc. Med Guide Revision Date July 2012), Tratuzuman Kd=8.2 nM (Costantini et al., 2007) and Erbitux Kd=0.2 nM (Product Monograph, Bristol-Myers Squibb Canada, December 2012).

Example 13

Recombinant Cloning; Testing of Human/Mouse Chimeric Variants of OI-3, CHOI-3.1 (IgG1) and CHOI-3.3 (IgG3)

A: Recombinant plasmids were constructed encoding heavy (SEQ ID NO:1 and 3) and light chain (SEQ ID NO:2 and 4) of OI-3 in combination with constant regions of human IgG/κ light chain (SEQ ID NO:5) and IgG1/κ (SEQ ID NO:6) or IgG3/κ (SEQ ID NO:7). The plasmids were transiently transfected into suspension CHO cell cultures.

The target antibodies, CHOI-3.1 and CHOI-3.3, were captured from the cell culture supernatant by HiTrap™ ProteinA HP 5 ml column. Analysis of antibodies by reduced and non-reduced SDS-PAGE and Western confirmed estimated molecular weight of ~55 kDa heavy chain, ~25 kDa light chain and ~150 kDa full length antibodies, respectively.

hIgG/κ light chain constant region
SEQ ID NO: 5
CGAACTGTGGCTGCACCATCTGTCTTCATCTTCCCGCCATCTGAT

GAGCAGTTGAAATCTGGAACTGCCTCTGTTGTGTGCCTGCTGAAT

AACTTCTATCCCAGAGAGGCAAAGTACAGTGGAAGGTGGATAAC

GCCCTCCAATCGGGTAACTCCCAGGAGAGTGTCACAGAGCAGGAC

AGCAAGGACAGCACCTACAGCCTCAGCAGCACCCTGACGCTGAGC

AAAGCAGACTACGAGAAACACAAAGTCTACGCCTGCGAAGTCACC

CATCAGGGCCTGAGCTCGCCCGTCACAAAGAGCTTCAACAGGGGA

GAGTGT hIgG1/κ heavy chain constant region
SEQ ID NO: 6
GCCTCCACCAAGGGACCAAGCGTGTTCCCACTGGCTCCATCTAGT

AAAAGTACTTCAGGGGGAACCGCCGCTCTGGGATGTCTGGTGAAG

GATTATTTCCCAGAGCCCGTGACAGTGAGCTGGAACTCCGGCGCC

CTGACCTCCGGAGTGCACACATTTCCAGCTGTGCTGCAGTCAAGC

GGCCTGTACTCTCTGTCCTCTGTGGTGACCGTGCCCAGTTCAAGC

CTGGGGACTCAGACCTATATCTGCAACGTGAATCACAAGCCAAGT

AATACAAAAGTGGACAAGAAAGTGGAACCCAAGAGCTGTGATAAA

ACACATACTTGCCCCCCTTGTCCTGCTCCAGAGCTGCTGGGAGGA

CCAAGCGTGTTCCTGTTTCCACCCAAGCCTAAAGACACCCTGATG

ATTTCCAGGACACCCGAAGTGACTTGCGTGGTGGTGGACGTGTCT

CACGAGGATCCTGAAGTGAAGTTCAACTGGTACGTGGATGGCGTG

GAGGTGCATAATGCCAAGACCAAACCCAGGGAGGAACAGTACAAT

AGCACCTATCGCGTGGTGTCCGTGCTGACAGTGCTGCACCAGGAC

TGGCTGAACGGCAAAGAGTATAAGTGCAAAGTGAGCAATAAGGCC

CTGCCCGCTCCTATCGAGAAAACAATTAGCAAGGCCAAAGGGCAG

CCTCGGGAACCACAGGTGTACACTCTGCCTCCATCCAGAGACGAG

CTGACAAAGAACCAGGTGTCTCTGACTTGTCTGGTGAAAGGGTTC

TATCCTTCAGATATTGCTGTGGAGTGGGAAAGCAATGGACAGCCA

GAAAACAATTACAAGACCACACCCCCTGTGCTGGACTCTGATGGA

AGTTTCTTTCTGTATTCTAAGCTGACTGTGGATAAAAGTCGGTGG

CAGCAGGGCAACGTGTTTAGCTGTTCCGTGATGCATGAGGCCCTG

CACAATCATTACACCCAGAAGTCTCTGAGTCTGTCACCTGGCAAA hIgG3/κ heavy chain constant region
SEQ ID NO: 7
GCTAGCACCAAGGGCCCATCGGTCTTCCCCCTGGCGCCCTGCTCC

AGGAGCACCCCTGGGGGCACAGCGGCCCTGGGCTGCCTGGTCAAG

GACTACTTCCCCGAACCGGTGACGGTGTCGTGGAACTCAGGCGCC

CTGACCAGCGGCGTGCACACCTTCCCGGCTGTCCTACAGTCCTCA

GGACTCTACTCCCTCAGCAGCGTGGTGACCGTGCCCTCCAGCAGC

TTGGGCACCCAGACCTACACCTGCAACGTGAATCACAAGCCCAGC

AACACCAAGGTGGACAAGAGAGTTGAGCTCAAAACCCCACTTGGT

GACACAACTCACACATGCCCACGGTGCCCAGAGCCCAAATCTTGT

GACACACCTCCCCCATGCCCACGGTGCCCAGCACCTGAACTCCTG

GGAGGACCGTCAGTCTTCCTCTTCCCCCCAAAACCCAAGGATACC

CTTATGATTTCCCGGACCCCTGAGGTCACGTGCGTGGTGGTGGAC

GTGAGCCACGAAGACCCCGAGGTCCAGTTCAAGTGGTACGTGGAC

GGCGTGGAGGTGCATAATGCCAAGACAAAGCCGCGGGAGGAGCAG

TTCAACAGCACGTTCCGTGTGGTCAGCGTCCTCACCGTCCTGCAC

CAGGACTGGCTGAACGGCAAGGAGTACAAGTGCAAGGTCTCCAAC

AAAGCCCTCCCAGCCCCCATCGAGAAAACCATCTCCAAACCCAAA

GGACAGCCCCGAGAACCACAGGTGTACACCCTGCCCCCATCCCGG

GAGGAGATGACCAAGAACCAGGTCAGCCTGACCTGCCTGGTCAAA

GGCTTCTACCCCAGCGACATCGCCGTGGAGTGGGAGAGCAGCGGG

CAGCCGGAGAACAACTACAACACCACGCCTCCCATGCTGGACTCC

GACGGCTCCTTCTTCCTCTACAGCAAGCTCACCGTGGACAAGAGC

AGGTGGCAGCAGGGGAACGTCTTCTCATGCTCCGTGATGCATGAG

GCTCTGCACAACCACTACACGCAGAAGAGCCTCTCCCTGTCTCCG

GGTAAA

B: Analysis of CHOI-3.1 and CHOI-3.3 binding specificity to melanoma cell line: To verify that the chimeric variants of OI-3 have equal binding properties as the murine OI-3, analyses of binding were performed. Flow cytometry analysis of equal batches of MelJRpost3.3 melanoma cells incubated with either 20, 10 or 5 μg/ml of CHOI-3.1 or CHOI-3.3 followed by wash and incubation with PE-conjugated anti-human IgG antibody (Fc gamma-specific, eBioscience) were conducted. Protocol for cultivation of cells and flow cytometry; see Example 4. CHOI-3.1 or CHOI-3.3 showed specific binding to the melanoma cell line (FIG. 8).

C: Blocking experiment using CHOI-3.1 and CHOI-3.3 to block $^{125}$I-OI-3: The human cancer cells lines MelJRpost 3.3 (melanoma) was used to study blocking of OI-3 by the CHOI-3.1 and CHOI-3.3. As an antigen negative control, the murine monoclonal IgG1, HH1, against human CD37 was used.

The cell lines were grown as monolayers in plastic flasks supplied with RPMI 1640 medium/fetal calf serum etc and kept in 5% CO2 incubators. After trypzinisation, cells were centrifuged, the supernatant removed and the cells re-suspended in Dulbecco's PBS with 0.5% bovine serum albumin (DPBS/BSA). Cell concentration was adjusted to approximately 10 million cells per ml.

Two-hundred microliter cell suspension was added to 4 ml reactions tubes. To duplicates were added either HH1 irrelevant IgG or 1 microgram each of CHOI-3.1 or CHOI-3.3. Each tube was whirl-mixed for 5 seconds and then put on a shaker for approximately 20 minutes to pre-saturate the antigen.

Thereafter approximately 80 nanogram of $^{125}$I-labeled OI-3 was added to each tube. Thereafter each tube was whirl-mixed for 5 seconds, and incubated on a shaker for 1-2 hours. After that each tube was counted on a gamma counter to determine applied activity, washed tree times with 0.5 ml DPBS/BSA and recounted for determining cell bound fraction.

The data (Table 4) shows that the two chimeric versions of OI-3 blocks binding of $^{125}$I-OI-3 effectively and in similar fashion as that found with pre- and co-treatment with the original murine OI-3. It should be noted that complete blocking is not expected with the used antibody concentration of about 5 µg/ml in this assay. This verifies that the chimeric versions were targeting the same epitope as the original OI-3 antibody.

TABLE 4

Binding of $^{125}$I-OI-3 to MelJRpost3.3 melanoma cells after pre-and co-treatment with antibodies.

| Pretreatment | HH1 (irrelevant) | CHOI-3.1 | CHOI-3.3 |
|---|---|---|---|
| Relative bound fraction* | 100% | 21.6% | 19.5% |

*Data for $^{125}$I-OI-3 and HH1 irrelevant IgG was normalized to 100%.

D: Cell binding fraction of radiolabeled chimeric versions of the OI-3: CHOI-3.1 and CHOI-3.3 were radiolabeled with $^{125}$I according to the procedures described in Example 7. The cell binding fractions were determined according to Example 8: The human cancer cells line Mel 3.3 (melanoma) was used to study binding of radiolabeled CHOI-3.1 and CHOI-3.3 monoclonal antibodies.

The cell line was grown as monolayers in plastic flasks supplied with RPMI 1640 medium/fetal calf serum etc and kept in 5% CO2 incubators. After trypzinisation, cells were centrifuged, the supernatant removed and the cells resuspended in Dulbecco's PBS with 0.5% bovine serum albumin (DPBS/BSA).

Cell concentrations were adjusted to 40 million cells per ml. One-hundred and eighty µl cell suspension was added to 4 ml reactions tubes. To duplicates were added 20 µl of DPBS/BSA or 20 µl OI-3 (1.2 mg/ml) as antigen-blocking. Each tube was whirl-mixed for 5 seconds and then incubated on a shaker for approximately 20 minutes to pre-saturate the antigen.

Thereafter approximately 2.1 nanogram of $^{125}$I-labeled CHOI-3.1 or 4.5 nanogram of $^{125}$I-labeled CHOI-3.3 was added to each tube. Thereafter each tube was whirlmixed for 5 seconds, and incubated at a shaker for 1.5 hours.

After that, each tube was counted on a gamma counter to determine applied activity, washed tree times with 0.5 ml DPBS/BSA and recounted for determining cell bound fraction.

It was assumed that the blocked cells represented the non-specific binding. The net cell-binding was calculated as total bound−non-specific bound. The net cell bound activity was thus determined to be 58% and 61% respectively for $^{125}$I-CHOI-3.1 and $^{125}$I-CHOI-3.3.

In conclusion: These results are in good agreement with that found for radiolabeled OI-3 in this assay showing that the OI-3 hybridoma/antibody platform is well suited to be used in generation of recombinant antibodies and derivatives.

E: Ability of chimeric OI-3 clones to recruit human natural killer cells for in vitro tumor cell kill: Antibody Dependent Cellular Cytotoxicity (ADCC) assays were conducted with 51Cr labelled target cells (WM239, human melanoma): The cells were grown in tissue culture flasks (175 cm$^2$) using RPMI-1640 (Hyclone, Thermo Scientific, USA), supplemented with 10% heat-inactivated fetal bovine serum (PAA, Thermo Scientific, USA). The cultures were harvested by trypsination followed by centrifugation (1200 rpm) for 5 min. Cell pellet was resuspended in assay medium (RPMI, 10% FCS) and cell count determined. Cell concentration was adjusted to 5×10$^6$/ml for labeling with chromium-51. 5×10$^6$ WM239 cells were labeled with 3, 7 MBq chromium-51 ($^{51}$Cr) (PerkinElmer, Netherlands) in a volume of 1 ml at 37° C. for 1 hour. The labeled cells were washed three times in DPBS with 2% FCS three times by centrifugation (2000 rpm at 5 min). The labeled cells are aliquoted in equal volumes for binding of OI-3, (batch: 3278) CHOI-3.1 (batch: 176799-1), CHOI-3.3 (batch: 176799-4) including a control with no antibody present. All samples are incubated at 37° C. for 10 min, and then washed twice in DPBS with 2% FCS three times by centrifugation (2000 rpm at 5 min).

Effector cells: Approximately 30 ml whole blood drawn on EDTA glass from healthy donor was used for the isolation of peripheral blood mononuclear cells (PBMC). Whole blood was diluted 1:1 with DPBS (DPBS, Hyclone, Thermo Scientific, USA) in a 50 ml tube. Diluted whole blood was layered on top of Lymphoprep (Medinor, Norway) in a ratio 2:1 in a 50 ml tube and centrifuged at 1000×g for 20 min with slow braking. The mononuclear cells from the interface are aspirated and washed twice with DPBS (300×g, 10 min). The pelleted cells are gently resuspended in culture medium (RPMI-1640 with 10% heat-inactivated fetal bovine serum) using a pipette and the cell count is determined in the cell counter. NK cells are isolated by depletion of non-NK cells from PBMC by Dynabeads Untouched Human NK cells (Invitrogen), following the manufactures protocol, and used as effector cells in the assay. NK cells are stimulated/or not with human recombinant interleukin-2 (25 ng/ml, eBiosciences) for 2-3 hours before initiating the ADCC assay.

ADCC: The target cells are cultivated with effector cells in a ratio of 20:1 in 96-well round-bottom microtiter plates in a final volume of 200 µl. First 10.000 target cells in a volume of 100 µl in assay medium are plated, followed by human NK-cells (ADCC) in a volume of 100 µl. As controls, target cells are cultivated in assay medium alone (spontaneous lysis) and in assay medium supplemented with 1% Triton X-100 (maximal lysis; total release). All samples are run in triplicates. The co-culture is incubated at 37° C. in a humid $CO_2$ incubator for 4 hours. The cytotoxic effect is measured by $^{51}$Cr release into the supernatant. At the end of the incubation cells are removed from the culture medium by centrifugation (1500 rpm; 5 min) at room temperature. Cell free supernatants (150 µl/well) are transferred into 96 corresponding 0.2 ml micro tubes. The amount of $^{51}$Cr released was measured by a gamma counter (Cobra II, Packard, land). % specific lysis is calculated with the following equation: 100×(experimental release−spontaneous release)/(totalt release−spontaneous release). Experimental release being the mean value of the replicates of a sample treatment. Triplicate samples for spontane release and totale release are run for each antibody treatment group, and the mean values are used for the experimental samples of the respective antibody treatment. The results shown in Table 5 shows that the chimeric OI-3 variants, CHOI-3.1 and CHOI-3.3 are able to mediate antibody dependent cytotoxity by human immune effector cells. Non-stimulated NK cells mediate no kill of the target cells when they have not been treated with antibody (no mAb), or when they have been treated with an irrelevant chimeric antibody (cetuximab, not binding WM239), wheras they mediate a 15% specific lysis when the target cells are pre-treated with either CHOI-3.1 or CHOI.3.3. When the NK cells have been treated with IL-2 in advance, the level of specific lysis auguments considerable (58-60%), indicating that the activity status of the NK cells are of importance as expected for ADCC activity. IL-2 stimulation also augument the antibody independent target cell kill as seen by the specific lysis (32-36%) seen in samples treated with no mAb or with cetuximab.

TABLE 5

Antibody Dependent Cellular Cytotoxity assay, % specific lysis mediated by antibody treatment of target cells (melanoma cell line WM239) by effector cells (NK cells, w/wo IL-2 stimulation).

| mAb treatment | non-stimulated NK cells | IL-2 stimulated NK cells |
|---|---|---|
| no mAb | 1% | 36% |
| CHOI-3.1 | 15% | 58% |
| CHOI-3.3 | 16% | 60% |
| Cetuximab | 0% | 32% |

Example 14

Biodistribution of $^{125}$I Labelled OI-3 in NUDE Mice with s.c. OHS Tumors

The ability of OI-3 to target tumor tissues in vivo was elevated in nude mice with subcutaneous xenografted OHS tumors. The labelling of antibodies was carried out as in Example 7: Both murine OI-3, the chimeric versions of OI-3 (CHOI-3.1 and CHOI-3.3) was included in the study. Epidermal growth factor receptor (EGFR) antibody Cetuximab is known to bind to OHS and was used as a positive control in the study, along with the irrelevant CD37 targeting HH1 antibody used as a negative control. 0.2-1 MBq of labelled antibody was injected in the tail vein of each mice. Animals was euthanized 24 hours after injection and tissues collected, weighed and measured on a Cobrall for level of activity. 4-5 mice were included for each antibody examined. The results are shown in Table 6.

TABLE 6

Tissue to blood radioactivity ratios at 24 h after injection of 125I labelled antibodies in nude mice carrying OHS xenografts. Percentage of injected dose pr gram tissue was calculated.

| Tissue:blood | OI-3 | CHOI-3.1 | CHOI-3.3 | Cetuximab | HH1 |
|---|---|---|---|---|---|
| Tumor:blood | 1.04 | 1.30 | 1.10 | 0.97 | 0.34 |
| Spleen:blood | 0.18 | 0.48 | 0.29 | 0.45 | 0.23 |
| Liver:blood | 0.23 | 0.46 | 0.29 | 0.67 | 0.36 |
| Kidney:blood | 0.32 | 0.33 | 0.31 | 0.39 | 0.23 |

It is shown that the OI-3 and the Chimeric OI-3 versions tested all had significant tumor targeting abilities in vivo, which is an essential feature for development of anticancer monoclonal antibodies or conjugates thereof. It confirms that the epitope combining properties of OI-3 is relevant for in vivo use. Compared with radiolabeled Cetuximab that targets EGFR and the antigen negative control, radiolabeled HH1, radiolabeled OI-3 variants all had better tumor to blood ratios. This confirms that OI-3 and derivatives have promising tumor targeting properties in vivo.

Example 15

Biodistribution of $^{177}$l Labelled OI-3 in NUDE Mice with s.c. OHS Tumors

The distribution of radioactivity in various tissues as a function of time after administration of the $^{177}$Lu-labeled OI-3 antibodies was examined. FIG. 9. The antibodies were labeled as described in Example 1. Antibodies were injected at dosages between 2-19 ug pr mouse (with activities in the range of 150-1200 kBq/mouse). No significant difference in the in vivo distribution kinetics of the OI-3 antibody variants is detected. All conjugates are rapidly absorbed in most tissues, including the tumors. The radioactivity in the tumors increased up to 4 days after injection, with a maximum between 2 and 4 days, whereas the uptake in normal tissues decrease or remain essentially unchanged during the same course of time. The chimeric IgG1 variant had the highest tumor uptake, with a maximum measured uptake of slightly above 20% ID/g at day 4. As expected, activity levels in blood peak at the first time point, before it declines markedly. Note that the uptake in femur and skull was low, indicating no free $^{177}$Lu, i.e. all radioimmunoconjugates had a high stability in vivo.

Example 16

Delay of Tumor Growth in Xenograft Mice with $^{177}$Lu Labelled CHOI-3.1

A small-scale study was carried out to assess the effect of $^{177}$Lu-CHOI-3.1 on the growth of OHS xenografts in nude mice. One week after implantation, mice were injected intravenously with 100 μl NaCl (control group, N=5) or 400 MBq/kg $^{177}$Lu-CHOI-3.1 (N=4). Tumor growth was determined by measuring the tumor diameters with a caliper. An ellipsoid shape were assumed and tumor volumes were calculated as $$V = \frac{a^2 b}{2},$$

were a and b are the short and long tumor diameters respectively. The xenografts had volumes from 45-200 mm$^3$ at the start of the study, and tumor size was measured 3 times a week for up to 3 weeks after injection. Thereafter measurements were done twice a week unless more frequent inspection was needed. Animals were euthanized by cervical dislocation if the largest tumor diameter approached 20 mm, body weight decreased 20% from baseline, or mice otherwise showed symptoms of disease and discomfort. FIG. 10 Show that the treated animals had a delay of time to 10-doubling of tumor volume compared to the control.

Example 17

$^{177}$Lu-OI-3 Exposure of Cells and Effect on Antigen Expression

The cell line MDA-MB-231 was plated in 25 cm$^2$ flasks supplied with 5 ml culture medium. The flask were added 150 μl of A: PBS/0.5% BSA buffer or B: 150 μl of A (PBS/0.5% BSA buffer) with 20 μg of OI-3 monoclonal antibody or C: 150 μl of A (PBS/0.5% BSA buffer) with 20 μg and 0.7 MBq of $^{177}$Lu-OI-3. The flasks were kept in a CO$^2$ incubator for three days, cells were washed and trypsinated and dissolved in PBS/0.5% BSA. The cell number/ml was determined and 1.6 μg/ml of $^{125}$I-Herceptin was added to assess binding to HER-2 antigen. Applied activity was measured using a gamma counter. After 1 hour of shaking at room temperature cells were centrifuged three times and washed with 0.5 ml DPBS/BSA. Thereafter, the cells were counted on the gamma counter and the $^{125}$I count numbers adjusted for spill over from $^{177}$Lu. The nonspecific binding of $^{125}$I-Herceptin to empty tubes were also subtracted from the count numbers. Results are shown in Table 7.

The cell binding of $^{125}$I-Herceptin was significantly increased in the cells treated with $^{125}$I-OI-3 compared with controls and cold OI-3 antibody, indicating antigen upregulation for HER-2. Conclusion: Treatment with radiolabeled OI-3 can improve subsequent targeting with antibody against co-expressed antigens on tumor cells.

TABLE 7

Uptake of $^{125}$I-Herceptin on cancer cells co-expressing CD146 and HER-2.

| Pre-treatment | Mean (percent bound vs. control) | Range (percent bound vs. mean of controls) |
| --- | --- | --- |
| DPBS/BSA (0.5%) | 100 | 97.0-103.0 |
| DPBS/BSA (0.5%) + 4 µg/ml OI-3 | 118 | 101.7-134.6 |
| DPBS/BSA (0.5%) + 4 µg/ml OI-3 radiolabeled with $^{177}$Lu | 149 | 140.6-156.7 |

REFERENCES

Aldovini D, Demichelis F, Doglioni C, Di Vizio D, Galligioni E, Brugnara S, Zeni B, Griso C, Pegoraro C, Zannoni M, Gariboldi M, Balladore E, Mezzanzanica D, Canevari S, Barbareschi M.M-CAM expression as marker of poor prognosis in epithelial ovarian cancer. Int J Cancer. 2006 Oct. 15; 119(8):1920-6.

Bardin N, Reumaux D, Geboes K, Colombel J F, Blot-Chabaud M, Sampol J, Duthilleul P, Dignat-George F. Increased expression of CD146, a new marker of the endothelial junction in active inflammatory bowel disease. Inflamm Bowel Dis. 2006 January; 12(1):16-21.

Bidlingmaier S, He J, Wang Y, An F, Feng J, Barbone D, Gao D, Franc B, Broaddus V C, Liu B. Identification of MCAM/CD146 as the target antigen of a human monoclonal antibody that recognizes both epithelioid and sarcomatoid types of mesothelioma. Cancer Res. 2009 Feb. 15; 69(4):1570-7.

Bruland O, Fodstad O, Pihl A. The use of multicellular spheroids in establishing human sarcoma cell lines in vitro. Int J Cancer. 1985 Jun. 15; 35(6):793-8.

Bruland O S, Fodstad O, Stenwig A E, Pihl A. Expression and characteristics of a novel human osteosarcoma-associated cell surface antigen. Cancer Res. 1988 Sep. 15; 48(18):5302-9.

Costantini D L, Chan C, Cai Z, Vallis K A, Reilly R M. (111)In-labeled trastuzumab (Herceptin) modified with nuclear localization sequences (NLS): an Auger electron-emitting radiotherapeutic agent for HER2/neu-amplified breast cancer. J Nucl Med. 2007 August; 48(8):1357-68.

Elgström E, Ohlsson T G, Tennvall J, Nilsson R. Pattern of antigen expression in metastases after radioimmunotherapy of a syngeneic rat colon carcinoma utilizing the BR96 antibody. Exp Hematol Oncol. 2012 Nov. 13; 1(1):34.

Esteban J M, Kuhn J A, Felder B, Wong J Y, Battifora H, Beatty J D, Wanek P M, Shively J E. Carcinoembryonic antigen expression of resurgent human colon carcinoma after treatment with therapeutic doses of 90Y-alpha-carcinoembryonic antigen monoclonal antibody. Cancer Res. 1991 Jul. 15; 51(14):3802-6.

Filshie R J, Zannettino A C, Makrynikola V, Gronthos S, Henniker A J, Bendall L J, Gottlieb D J, Simmons P J, Bradstock K F. MUC18, a member of the immunoglobulin superfamily, is expressed on bone marrow fibroblasts and a subset of hematological malignancies. Leukemia. 1998 March; 12(3):414-21.

Fodstad O, Brøgger A, Bruland O, Solheim O P, Nesland J M, Pihl A. Characteristics of a cell line established from a patient with multiple osteosarcoma, appearing 13 years after treatment for bilateral retinoblastoma. Int J Cancer. 1986 Jul. 15; 38(1): 33-40.

Godal A, Bruland O, Haug E, Aas M, Fodstad O. Unexpected expression of the 250 kD melanoma-associated antigen in human sarcoma cells. Br J Cancer. 1986 June; 53(6):839-41.

Harputluoglu H, Dizdar O, Altundag K. Potential targeted therapy options in the management of basal cell subtype of breast carcinoma. Hum Pathol. 2007 December; 38(12):1869; author reply 1870.

Hemminki A, Hoffrén A M, Takkinen K, Vehniäinen M, Mäkinen M L, Pettersson K, Teleman O, Söderlund H, Teeri T T. Introduction of lysine residues on the light chain constant domain improves the labelling properties of a recombinant Fab fragment. Protein Eng. 1995 February; 8(2):185-91.

Herlyn M. Human melanoma: development and progression. Cancer Metastasis Rev. 1990 September; 9(2):101-12.

Iyer A K, Su Y, Feng J, Lan X, Zhu X, Liu Y, Gao D, Seo Y, Vanbrocklin H F, Courtney Broaddus V, Liu B, He J. The effect of internalizing human single chain antibody fragment on liposome targeting to epithelioid and sarcomatoid mesothelioma. Biomaterials. 2011 April; 32(10): 2605-13.

Jiang T, Zhuang J, Duan H, Luo Y, Zeng Q, Fan K, Yan H, Lu D, Ye Z, Hao J, Feng J, Yang D, Yan X. CD146 is a coreceptor for VEGFR-2 in tumor angiogenesis. Blood. 2012 Sep. 13; 120(11):2330-9.

Kristiansen G, Yu Y, Schlüns K, Sers C, Dietel M, Petersen I. Expression of the cell adhesion molecule CD146/MCAM in non-small cell lung cancer. Anal Cell Pathol. 2003; 25(2):77-81.

Lai F, Jiang C C, Farrelly M L, Zhang X D, Hersey P. Evidence for upregulation of Bim and the splicing factor SRp55 in melanoma cells from patients treated with selective BRAF inhibitors. Melanoma Res. 2012 June; 22(3):244-51.

Lehmann J M, Holzmann B, Breitbart E W, Schmiegelow P, Riethmüller G, Johnson J P. Discrimination between benign and malignant cells of melanocytic lineage by two novel antigens, a glycoprotein with a molecular weight of 113,000 and a protein with a molecular weight of 76,000. Cancer Res. 1987 Feb. 1; 47(3):841-5.

Lehmann J M, Riethmüller G, Johnson J P. MUC18, a marker of tumor progression in human melanoma, shows sequence similarity to the neural cell adhesion molecules of the immunoglobulin superfamily. Proc Natl Acad Sci USA. 1989 December; 86(24):9891-5.

Ma X, Liu J, Wu J, Yan X, Wu P, Liu Y, Li S, Tian Y, Cao Y, Chen G, Meng L, Xu G, Wang S, Lu Y, Ma D, Zhou J. Synergistic killing effect between vorinostat and target of CD146 in malignant cells. Clin Cancer Res. 2010 Nov. 1; 16(21):5165-76.

McGary E C, Heimberger A, Mills L, Weber K, Thomas G W, Shtivelband M, Lev D C, Bar-Eli M. A fully human antimelanoma cellular adhesion molecule/MUC18 antibody inhibits spontaneous pulmonary metastasis of osteosarcoma cells in vivo. Clin Cancer Res. 2003 Dec. 15; 9(17):6560-6.

Melnikova V O, Bar-Eli M. Bioimmunotherapy for melanoma using fully human antibodies targeting MCAM/MUC18 and IL-8. Pigment Cell Res. 2006 October; 19(5):395-405.

Middleton J, Americh L, Gayon R, Julien D, Mansat M, Mansat P, Anract P, Cantagrel A, Cattan P, Reimund J M, Aguilar L, Amalric F, Girard J P. A comparative study of endothelial cell markers expressed in chronically inflamed human tissues: MECA-79, Duffy antigen receptor for chemokines, von Willebrand factor, CD31, CD34, CD105 and CD146. J Pathol. 2005 July; 206(3):260-8.

Orbom A, Eriksson S E, Elgström E, Ohlsson T, Nilsson R, Tennvall J, Strand S E. The Intratumoral Distribution of Radiolabeled 177Lu-BR96 Monoclonal Antibodies Changes in Relation to Tumor Histology over Time in a Syngeneic Rat Colon Carcinoma Model. J Nucl Med. 2013 August; 54(8):1404-10.

Peer D, Karp J M, Hong S, Farokhzad O C, Margalit R, Langer R. Nanocarriers as an emerging platform for cancer therapy. Nat Nanotechnol. 2007 December; 2(12): 751-60.

Pickl W F, Majdic O, Fischer G F, Petzelbauer P, Faé I, Waclavicek M, Stöckl J, Scheinecker C, Vidicki T, Aschauer H, Johnson J P, Knapp W. MUC18/MCAM (CD146), an activation antigen of human T lymphocytes. J Immunol. 1997 Mar. 1; 158(5):2107-15.

Raja C, Graham P, Abbas Rizvi S M, Song E, Goldsmith H, Thompson J, Bosserhoff A, Morgenstern A, Apostolidis C, Kearsley J, Reisfeld R, Allen B J. Interim analysis of toxicity and response in phase 1 trial of systemic targeted alpha therapy for metastatic melanoma. Cancer Biol Ther. 2007 June; 6(6):846-52.

Schlom J, Molinolo A, Simpson J F, Siler K, Roselli M, Hinkle G, Houchens D P, Colcher D. Advantage of dose fractionation in monoclonal antibody-targeted radioimmunotherapy. J Natl Cancer Inst. 1990 May 2; 82(9):763-71.

Sers C, Riethmüller G, Johnson J P. MUC18, a melanoma-progression associated molecule, and its potential role in tumor vascularization and hematogenous spread. Cancer Res. 1994 Nov. 1; 54(21):5689-94.

Shih I M, Nesbit M, Herlyn M, Kurman R J. A new Mel-CAM (CD146)-specific monoclonal antibody, MN-4, on paraffin-embedded tissue. Mod Pathol. 1998 November; 11(11):1098-106.

Sievers E L, Senter P D. Antibody-drug conjugates in cancer therapy. Annu Rev Med. 2013; 64:15-29.

Singh S, Sharma A, Robertson G P. Realizing the clinical potential of cancer nanotechnology by minimizing toxicologic and targeted delivery concerns. Cancer Res. 2012 Nov. 15; 72(22):5663-8.

Sinha R, Kim G J, Nie S, Shin D M. Nanotechnology in cancer therapeutics: bioconjugated nanoparticles for drug delivery. Mol Cancer Ther. 2006 August; 5(8): 1909-17.

Smeland E, Funderud S, Ruud E, Kiil Blomhoff H, Godal T. Characterization of two murine monoclonal antibodies reactive with human B cells. Their use in a high-yield, high-purity method for isolation of B cells and utilization of such cells in an assay for B-cell stimulating factor. Scand J Immunol. 1985 March; 21(3):205-14.

Voutsas I F, Mahaira L G, Fotopoulou K, Kapranos N, Reclos J G, Gritzapis A D, Papamichail M, Perez S A, Baxevanis C N. Gamma-irradiation induces HER-2/neu overexpression in breast cancer cell lines and sensitivity to treatment with trastuzumab. Int J Radiat Biol. 2013 May; 89(5):319-25.

Wang B, Chen Y B, Ayalon O, Bender J, Garen A. Human single-chain Fv immunoconjugates targeted to a melanoma-associated chondroitin sulfate proteoglycan mediate specific lysis of human melanoma cells by natural killer cells and complement. Proc Natl Acad Sci USA. 1999 Feb. 16; 96(4):1627-32.

Wang X, Osada T, Wang Y, Yu L, Sakakura K, Katayama A, McCarthy J B, Brufsky A, Chivukula M, Khoury T, Hsu D S, Barry W T, Lyerly H K, Clay T M, Ferrone S. CSPG4 protein as a new target for the antibody-based immunotherapy of triple-negative breast cancer. J Natl Cancer Inst. 2010 Oct. 6; 102(19):1496-512.

Wu G J, Wu M W, Wang S W, Liu Z, Qu P, Peng Q, Yang H, Varma V A, Sun Q C, Petros J A, Lim S D, Amin M B. Isolation and characterization of the major form of human MUC18 cDNA gene and correlation of MUC18 over-expression in prostate cancer cell lines and tissues with malignant progression. Gene. 2001 Nov. 14; 279(1): 17-31.

Zhang Y, Zheng C, Zhang J, Yang D, Feng J, Lu D, Yan X. Generation and characterization of a panel of monoclonal antibodies against distinct epitopes of human CD146. Hybridoma (Larchmt). 2008 October; 27(5):345-52.

The invention claimed is:

1. An antibody molecule that binds to human CD146, wherein said antibody is:
  a monoclonal antibody comprising:
  i) a heavy chain variable domain comprising the amino acid sequence shown in SEQ ID NO: 3; and
  ii) a light chain variable domain comprising the amino acid sequence shown in SEQ ID NO: 4.

2. The antibody of claim 1, wherein the monoclonal antibody is OI-3.

3. The antibody of claim 1, wherein said antibody molecule is a chimeric or a humanized antibody.

4. The antibody of claim 1, further comprising
  b) a linker, and
  c) a radionuclide selected from the group consisting of $^{211}$At, $^{213}$Bi, $^{212}$Bi, $^{212}$Pb, $^{225}$Ac, $^{227}$Th, $^{90}$Y, $^{186}$Re, $^{188}$Re, $^{199}$Au, $^{194}$Ir, $^{166}$Ho, $^{159}$Gd, $^{153}$Sm, $^{149}$Pm, $^{142}$Pr, $^{111}$Ag, $^{109}$Pd, $^{77}$As, $^{67}$Cu, $^{47}$Sc, $^{230}$U, $^{226}$Th, $^{223}$Ra, $^{224}$Ra, $^{225}$Ra, $^{131}$I, $^{18}$F, $^{64}$Cu, $^{67}$Ga, $^{99m}$Tc, $^{123}$I, $^{124}$I, $^{125}$I, $^{131}$I, $^{111}$In, $^{161}$Tb and $^{177}$Lu.

5. A method of inhibiting or treating a cancer comprising providing the antibody molecule of claim 1 to a subject in need thereof.

6. The method of claim 5, wherein the antibody that binds CD 146 further comprises a linker, and a radionuclide selected from the group consisting of $^{211}$At, $^{213}$Bi, $^{212}$Bi, $^{212}$Pb, $^{225}$Ac, $^{227}$Th, $^{90}$Y, $^{186}$Re, $^{188}$Re, $^{199}$Au, $^{194}$Ir, $^{166}$Ho, $^{159}$Gd, $^{153}$Sm, $^{149}$Pm, $^{142}$Pr, $^{111}$Ag, $^{109}$Pd, $^{77}$As, $^{67}$Cu, $^{47}$Sc, $^{230}$U, $^{226}$Th, $^{223}$Ra, $^{224}$Ra, $^{225}$Ra, $^{131}$I, $^{18}$F, $^{64}$Cu, $^{67}$Ga, $^{99m}$Tc, $^{123}$I, $^{124}$I, $^{125}$I, $^{131}$I, $^{111}$In, $^{161}$Tb and $^{177}$Lu.

7. A combination therapy for treating cancer from solid cancers comprising: administering to a subject in need thereof, the antibody according to claim 1 or a radioimmunoconjugate having the monoclonal antibody according to claim 1, and a monoclonal antibody or derivatives thereof specific for HER-2 or EGFR for treating cancer from solid cancers.

* * * * *